United States Patent
Müller et al.

(10) Patent No.: US 6,969,697 B2
(45) Date of Patent: Nov. 29, 2005

(54) SUBSTITUTED BENZOYLCYCLOHEXENONES

(75) Inventors: Klaus-Helmut Müller, Düsseldorf (DE); Hans-Georg Schwarz, Langenfeld (DE); Stefan Herrmann, Langenfeld (DE); Dorothee Hoischen, Düsseldorf (DE); Stefan Lehr, Langenfeld (DE); Otto Schallner, Monheim (DE); Mark Wilhelm Drewes, Langenfeld (DE); Peter Dahmen, Neuss (DE); Dieter Feucht, Monheim (DE); Rolf Pontzen, Leichlingen (DE); Akihiko Yanagi, Tochigi (JP); Shinichi Narabu, Ibaraki (JP); Toshio Goto, Tochigi (JP); Seishi Ito, Tochigi (JP); Chieko Ueno, Tochigi (JP)

(73) Assignees: Bayer Aktiengesellschaft, Leverkusen (DE); Nihon Bayer Agrochem K. K., Tokyo (JP)

( * ) Notice: Subject to any disclaimer, the term of this patent is extended or adjusted under 35 U.S.C. 154(b) by 45 days.

(21) Appl. No.: 10/220,711

(22) PCT Filed: Mar. 1, 2001

(86) PCT No.: PCT/EP01/02279

§ 371 (c)(1), (2), (4) Date: Oct. 21, 2002

(87) PCT Pub. No.: WO01/66527

PCT Pub. Date: Sep. 13, 2001

(65) Prior Publication Data

US 2004/0002599 A1 Jan. 1, 2004

(30) Foreign Application Priority Data

Mar. 6, 2000 (DE) ......... 100 10 937
Jun. 9, 2000 (DE) ......... 100 28 687

(51) Int. Cl.[7] ............... A01N 43/84; A01N 43/653; C07D 249/12; C07D 407/04
(52) U.S. Cl. ............... 504/225; 504/273; 548/263.2; 548/263.4; 548/263.8; 548/364.2; 544/132
(58) Field of Search ................ 504/273, 225; 548/263.2, 263.4, 263.8, 364.2; 544/132

(56) References Cited

U.S. PATENT DOCUMENTS

| | | | | |
|---|---|---|---|---|
| 5,977,376 A | * | 11/1999 | Araki et al. | 548/268.6 |
| 6,004,903 A | | 12/1999 | von Deyn et al. | 504/239 |
| 6,153,759 A | | 11/2000 | von Deyn et al. | 548/131 |

FOREIGN PATENT DOCUMENTS

| | | |
|---|---|---|
| DE | 199 21 732 | 1/2000 |
| EP | 0 135 191 | 10/1985 |
| EP | 0 186 120 | 11/1988 |
| EP | 0 186 119 | 8/1989 |
| EP | 0 186 118 | 5/1990 |
| EP | 0 090 262 | 8/1992 |
| EP | 0 319 075 | 7/1994 |
| WO | 97/46530 | 12/1997 |
| WO | 99/07688 | 2/1999 |

OTHER PUBLICATIONS

Chemical Abstracts, vol. 130, No. 14, 1999 Columbus, Ohio, US; abstract No. 178767w, Seite 223; Spalte 2; XP002174489 Zusammenfassung & JP 01 121280 A (Nippon Soda Jan. 26, 1999.

* cited by examiner

*Primary Examiner*—Joseph K. McKane
*Assistant Examiner*—Rebecca Anderson
(74) *Attorney, Agent, or Firm*—Richard E. L. Henderson; Raymond J. Harmuth

(57) ABSTRACT

The invention relates to novel substituted benzoylcyclohexenones of the formula (I),

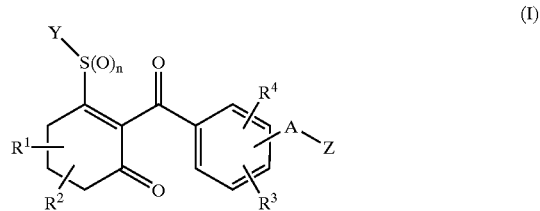

in which
n, A, $R^1$, $R^2$, $R^3$, $R^4$, Y and Z are each as defined in the description,
and also to processes for their preparation and to their use as herbicides.

16 Claims, No Drawings

SUBSTITUTED BENZOYLCYCLOHEXENONES

This application is a 371 of PCT/EP01/02279 filed Mar. 01, 2001.

The invention relates to novel substituted benzoylcyclohexenones, to processes for their preparation and to their use as herbicides.

It is already known that certain substituted benzoylcyclohexanediones have herbicidal properties (cf. EP-A-090 262, EP-A-135 191, EP-A-186 118, EP-A-186 119, EP-A-186 120, EP-A-319 075, WO-A-96/26200, WO-A-97/46530, WO-A-99/07688, WO-A-00/05221). However, the activity of these compounds is not in all respects satisfactory.

This invention, accordingly, provides the novel substituted benzoylcyclohexenones of the formula (I),

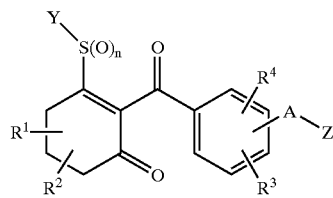

(I)

in which n represents the number 0, 1 or 2,

A represents a single bond or represents alkanediyl (alkylene) having 1 to 6 carbon atoms, $R^1$ represents hydrogen, phenyl or optionally cyano-, halogen-, $C_1$–$C_4$-alkoxy- or $C_1$–$C_4$-alkylthio-substituted alkyl having 1 to 6 carbon atoms, $R^2$ represents hydrogen or optionally cyano-, halogen-, $C_1$–$C_4$-alkoxy- or $C_1$–$C_4$-alkylthio -substituted alkyl having 1 to 6 carbon atoms, or together with $R^1$ represents alkanediyl (alkylene) having 1 to 6 carbon atoms, or together with $R^1$—in this case attached to the same carbon atom—and the carbon atom to which $R^1$ and $R^2$ are attached in this case represents a (C=O) grouping, $R^3$ represents hydrogen, nitro, cyano, carboxyl, carbamoyl, thiocarbamoyl, halogen, or represents in each case optionally cyano-, halogen- or $C_1$–$C_4$-alkoxy-substituted alkyl, alkoxy, alkylthio, alkylsulphinyl, alkylsulphonyl, alkylamino, dialkylamino or dialkylaminosulphonyl having in each case 1 to 6 carbon atoms in the alkyl groups, $R^4$ represents hydrogen, nitro, cyano, carboxyl, carbamoyl, thiocarbamoyl, halogen, or represents in each case optionally cyano-, halogen- or $C_1$–$C_4$-alkoxy-substituted alkyl, alkoxy, alkylthio, alkylsulphinyl, alkylsulphonyl, alkylamino, dialkylamino or dialkylaminosulphonyl having in each case 1 to 6 carbon atoms in the alkyl groups, and Y represents hydrogen, represents optionally cyano-, halogen- or $C_1$–$C_4$-alkoxy-substituted alkyl having 1 to 10 carbon atoms, represents in each case optionally cyano-, halogen-, $C_1$–$C_4$-alkyl-carbonyl- or $C_1$–$C_4$-alkoxy-carbonyl-substituted alkenyl or alkinyl having in each case 2 to 10 carbon atoms, or represents in each case optionally nitro-, amino-, cyano-, carboxyl-, carbamoyl-, thiocarbamoyl-, halogen-, $C_1$–$C_4$-alkyl-, $C_1$–$C_4$-halogenoalkyl-, $C_1$–$C_4$-alkoxy-$C_1$–$C_4$-alkyl-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkylsulphinyl-, $C_1$–$C_4$-halogenoalkylsulphinyl-, $C_1$–$C_4$-alkylsulphonyl-, $C_1$–$C_4$-halogenoalkylsulphonyl-, $C_1$–$C_4$-alkyl-carbonyl-, $C_1$–$C_4$-alkoxy-carbonyl-, $C_1$–$C_4$-alkyl-carbonyl-amino-, $C_1$–$C_4$-alkoxy-carbonyl-amino-, $C_1$–$C_4$-alkyl-sulphonyl-amino-substituted aryl or arylalkyl having in each case 6 or 10 carbon atoms in the aryl groups and optionally 1 to 4 carbon atoms in the alkyl moiety, and Z represents an optionally substituted 4- to 12-membered saturated or unsaturated, monocyclic or bicyclic, heterocyclic grouping which contains 1 to 4 hetero atoms (up to 4 nitrogen atoms and optionally—alternatively or additionally—one oxygen atom or one sulphur atom, or one SO grouping or one $SO_2$ grouping), and which contains additionally one to three oxo groups (C=O) and/or thioxo groups (C=S) as components of the heterocycle, including all possible tautomeric and, if appropriate, possible stereoisomeric forms of the compounds of the general formula (I), and the possible salts or metal-coordinated derivatives of the compounds of the general formula (I).

In the definitions, the hydrocarbon chains, such as alkyl or alkanediyl, are in each case straight-chain or branched—including in combination with heteroatoms, such as in alkoxy.

Preferred meanings of the radicals or groupings present in the formulae shown above and below are defined below.

n preferably represents the number 0 or 2.

A preferably represents a single bond or represents alkanediyl (alkylene) having 1 to 4 carbon atoms.

$R^1$ preferably represents hydrogen, phenyl or optionally cyano-, halogen-, $C_1$–$C_4$-alkoxy- or $C_1$–$C_4$-alkylthio-substituted alkyl having 1 to 5 carbon atoms.

$R^2$ preferably represents hydrogen or optionally cyano-, halogen-, $C_1$–$C_4$-alkoxy- or $C_1$–$C_4$-alkylthio-substituted alkyl having 1 to 5 carbon atoms, or together with $R^1$ represents alkanediyl (alkylene) having 1 to 5 carbon atoms.

$R^3$ preferably represents hydrogen, nitro, cyano, carboxyl, carbamoyl, thiocarbamoyl, halogen, or represents in each case optionally cyano-, halogen- or $C_1$–$C_4$-alkoxy-substituted alkyl, alkoxy, alkylthio, alkylsulphinyl, alkylsulphonyl, alkylamino, dialkylamino or dialkylaminosulphonyl having in each case 1 to 5 carbon atoms in the alkyl groups.

$R^4$ preferably represents hydrogen, nitro, cyano, carboxyl, carbamoyl, thiocarbamoyl, halogen, or represents in each case optionally cyano-, halogen- or $C_1$–$C_4$-alkoxy-substituted alkyl, alkoxy, alkylthio, alkylsulphinyl, alkylsulphonyl, alkylamino, dialkylamino or dialkylaminosulphonyl having in each case 1 to 5 carbon atoms in the alkyl groups.

Y preferably represents hydrogen, represents optionally cyano-, halogen- or $C_1$–$C_4$-alkoxy-substituted alkyl having 1 to 6 carbon atoms, represents in each case optionally cyano-, halogen-, $C_1$–$C_4$-alkyl-carbonyl- or $C_1$–$C_4$-alkoxy-carbonyl-substituted alkenyl or alkinyl having in each case 2 to 6 carbon atoms, or represents in each case optionally nitro-, amino-, cyano-, carboxyl-, carbamoyl-, thiocarbamoyl-, halogen-, $C_1$–$C_4$-alkyl-, $C_1$–$C_4$-halogenoalkyl-, $C_1$–$C_4$-alkoxy-$C_1$–$C_4$-alkyl-, $C_1$–$C_4$-alkoxy-, $C_1$–$C_4$-halogenoalkoxy-, $C_1$–$C_4$-alkylthio, $C_1$–$C_4$-halogenoalkylthio-, $C_1$–$C_4$-alkylsulphinyl-, $C_1$–$C_4$-halogeno-alkylsulphinyl-, $C_1$–$C_4$-alkylsulphonyl-, $C_1$–$C_4$-halogenoalkylsulphonyl-, $C_1$–$C_4$-alkyl-carbonyl-, $C_1$–$C_4$-alkoxy-carbonyl-, $C_1$–$C_4$-alkyl-carbonyl-amino-, $C_1$–$C_4$-alkoxy-carbonyl-amino-, $C_1$–$C_4$-alkyl-sulphonyl-amino-substituted aryl or arylalkyl having in each case 6 or 10 carbon atoms in the aryl groups and optionally 1 to 4 carbon atoms in the alkyl moiety.

Z preferably represents one of the heterocyclic groupings below

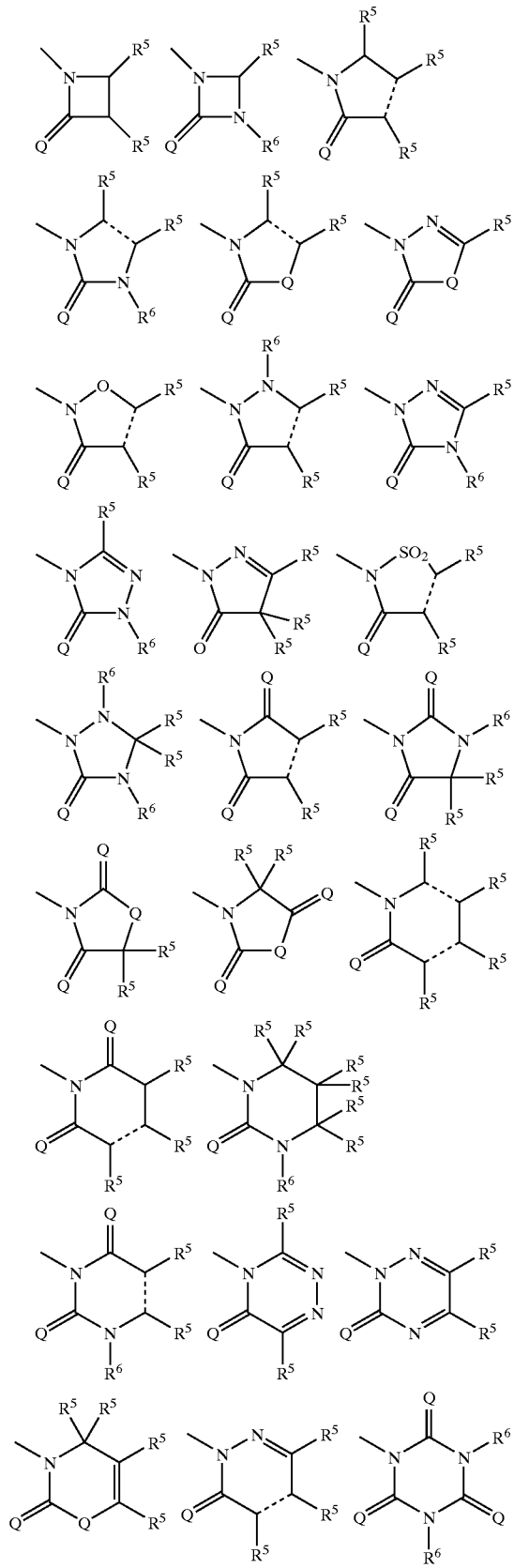
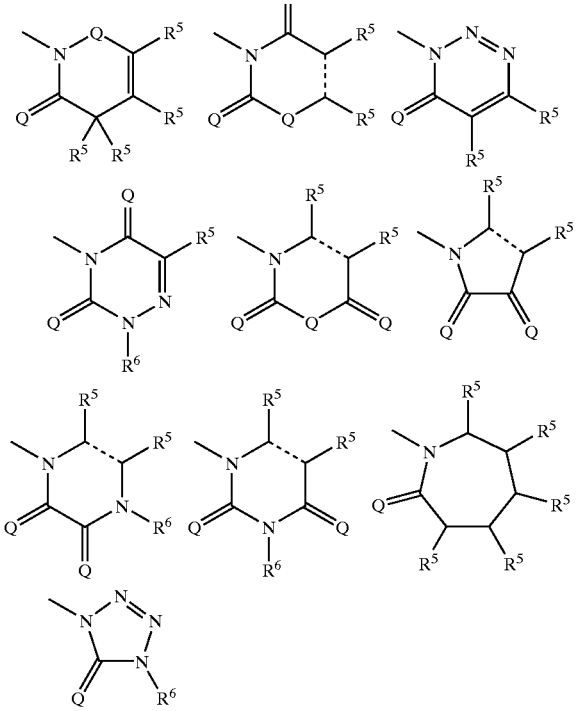

in which the bond drawn broken in each case denotes a single bond or a double bond, and in which each heterocycle preferably only carries two substituents of the definition $R^5$ and/or $R^6$ in any combination.

Q represents oxygen or sulphur, $R^5$ represents hydrogen, hydroxyl, mercapto, cyano, halogen, represents in each case optionally cyano-, halogen-, $C_1$–$C_4$-alkoxy-, $C_1$–$C_4$-alkylthio-, $C_1$–$C_4$-alkylsulphinyl- or $C_1$–$C_4$-alkylsulphonyl-substituted alkyl, alkylcarbonyl, alkoxy, alkoxycarbonyl, alkylthio, alkylsulphinyl or alkylsulphonyl having in each case up to 6 carbon atoms in the alkyl groups, represents in each case optionally halogen-substituted alkylamino or dialkylamino having in each case up to 6 carbon atoms in the alkyl groups, represents in each case optionally halogen-substituted alkenyl, alkinyl, alkenyloxy, alkenylthio, alkinylthio or alkenylamino having in each case up to 6 carbon atoms in the alkenyl or alkinyl groups, represents in each case optionally halogen-substituted cycloalkyl, cycloalkyloxy, cycloalkylthio, cycloalkylamino, cycloalkylalkyl, cycloalkylalkoxy, cycloalkylalkylthio or cycloalkylalkylamino having in each case 3 to 6 carbon atoms in the cycloalkyl groups and optionally up to 4 carbon atoms in the alkyl moiety, or represents in each case optionally halogen-, $C_1$–$C_4$-alkyl- or $C_1$–$C_4$-alkoxy-substituted phenyl, phenyloxy, phenylthio, phenylamino, benzyl, benzyloxy, benzylthio or benzylamino, represents pyrrolidino, piperidino or morpholino, or—if two adjacent radicals $R^5$ and $R^5$ are located at a double bond—also together with the adjacent radical $R^5$ represents a benzo grouping, and $R^6$ represents hydrogen, hydroxyl, amino, alkylideneamino having up to 4 carbon atoms, represents in each case optionally halogen- or $C_1$–$C_4$-alkoxy-substituted alkyl, alkoxy, alkylamino, dialkylamino or alkanoylamino having in each case up to 6 carbon atoms in the alkyl groups, represents in each case optionally halogen-substituted alkenyl, alkinyl or alkenyloxy having in each case up to 6 carbon atoms in the alkenyl or alkinyl groups, represents in each case optionally halogen-substituted cycloalkyl, cycloalkylalkyl or cycloalkylamino having in each case 3 to 6 carbon atoms in the cycloalkyl groups and optionally up to 3 carbon atoms in the alkyl moiety, or represents in each case optionally halogen-, $C_1$–$C_4$-alkyl- or $C_1$–$C_4$-alkoxy-substituted phenyl or benzyl, or together with an adjacent radical $R^5$ or $R^6$ represents optionally halogen- or $C_1$–$C_4$-alkyl-substituted alkanediyl having 3 to 5 carbon atoms, where the individual radicals $R^5$ and $R^6$—if two or more of them are attached to the same heterocyclic groupings— may have identical or different meanings in the context of the above definition.

n particularly preferably represents the number 0.

A particularly preferably represents a single bond or represents methylene, ethylidene (ethane-1,1-diyl) or dimethylene (ethane-1,2-diyl).

$R^1$ particularly preferably represents hydrogen, phenyl or in each case optionally cyano-, fluorine-, chlorine-, bromine-, methoxy-, ethoxy-, n- or i-propoxy-, methylthio-, ethylthio-, n- or i-propylthio-substituted methyl, ethyl, n- or i-propyl, n-, i- or s-butyl.

$R^2$ particularly preferably represents hydrogen or represents in each case optionally cyano-, fluorine-, chlorine-, bromine-, methoxy-, ethoxy-, n- or i-propoxy-, methylthio-, ethylthio-, n- or i-propylthio-substituted methyl, ethyl, n- or i-propyl, n-, i- or s-butyl, or together with $R^1$ represents methylene, ethylidene (ethane-1,1-diyl), dimethylene (ethane-1,2-diyl), propylidene (propane-1,1-diyl) or trimethylene (propane-1,3-diyl).

$R^3$ particularly preferably represents hydrogen, nitro, cyano, carboxyl, carbamoyl, thiocarbamoyl, fluorine, chlorine, bromine, iodine, or represents in each case optionally cyano-, fluorine-, chlorine-, bromine-, methoxy-, ethoxy-, n- or i-propoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, n-, i-, s- or t-butylamino, dimethylamino, diethylamino, dimethylaminosulphonyl or diethylaminosulphonyl.

$R^4$ particularly preferably represents hydrogen, nitro, cyano, carboxyl, carbamoyl, thiocarbamoyl, fluorine, chlorine, bromine, iodine, or represents in each case optionally cyano-, fluorine-, chlorine-, bromine-, methoxy-, ethoxy-, n- or i-propoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, n-, i-, s- or t-butylamino, dimethylamino, diethylamino, dimethylaminosulphonyl or diethylaminosulphonyl.

Y particularly preferably represents hydrogen, represents in each case optionally cyano-, fluorine-, chlorine-, bromine-, methoxy-, ethoxy-, n- or i-propoxy-substituted methyl, ethyl, n- or i-propyl, n-, i-, s- or t-butyl, represents in each case optionally cyano-, fluorine-, chlorine-, bromine-, acetyl-, propionyl-, n- or i-butyroyl-, methoxycarbonyl-, ethoxycarbonyl-, n- or i-propoxycarbonyl-substituted ethenyl, propenyl, butenyl, pentenyl, ethinyl, propinyl or butinyl, or represents in each case optionally nitro-, amino-, cyano-, carboxyl-, carbamoyl-, thiocarbamoyl-, fluorine-, chlorine-, bromine-, iodine-, methyl-, ethyl-, n- or i-propyl-, n-, i-, s- or t-butyl-, trifluoromethyl-, methoxymethyl-, ethoxymethyl-, methoxyethyl-, ethoxyethyl-, methoxy-, ethoxy-, n- or i-propoxy-, n-, i-, s- or t-butoxy-, difluoromethoxy-, trifluoromethoxy-, methylthio-, ethylthio-, n- or i-propylthio-, n-, i-, s- or t-butylthio-, difluoromethylthio-, trifluoromethylthio-, methylsulphinyl-, ethylsulphinyl-, trifluoromethylsulphinyl-, methylsulphonyl-, ethylsulphonyl-, trifluoromethylsulphonyl-, acetyl-, propionyl-, n- or i-butyroyl-, methoxycarbonyl-, ethoxycarbonyl-, n- or i-propoxycarbonyl-, acetylamino-, propionylamino-, methoxycarbonylamino-, ethoxycarbonylamino-, methylsulphonylamino-, ethylsulphonylamino-, n- or i-propylsulphonylamino-substituted phenyl, naphthyl, benzyl or phenylethyl.

Z particularly preferably represents one of the heterocyclic groupings below

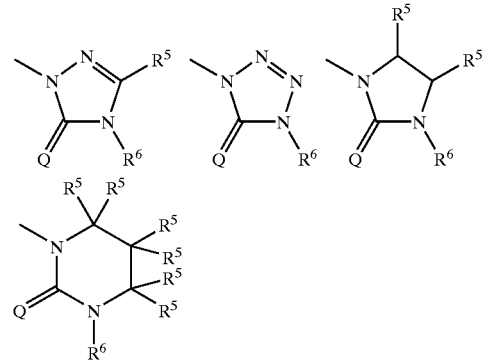

Q preferably represents oxygen, $R^5$ preferably represents hydrogen, hydroxyl, mercapto, cyano, fluorine, chlorine, bromine, iodine, represents in each case optionally fluorine-, chlorine-, methoxy-, ethoxy-, n- or i-propoxy-, n-, i-, s- or t-butoxy-, methylthio-, ethylthio-, n- or i-propylthio-, n-, i-, s- or t-butylthio-, methylsulphinyl-, ethylsulphinyl-, n- or i-propylsulphinyl-, methylsulphonyl-, ethylsulphonyl-, n- or i-propylsulphonyl-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, represents methylamino, ethylamino, n- or i-propylamino, n-, i-, s- or t-butylamino, dimethylamino, diethylamino, di-n-propylamino or di-i-propylamino, represents in each case optionally fluorine- and/or chlorine-substituted ethenyl, propenyl, butenyl, ethinyl, propinyl, butinyl, propenyloxy, butenyloxy, propenylthio, butenylthio, propenylamino or butenylamino, represents in each case optionally fluorine- and/or chlorine-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino, cyclohexylamino, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopropylmethylthio, cyclobutylmethylthio, cyclopentylmethylthio, cyclohexylmethylthio, cyclopropylmethylamino, cyclobutylmethylamino, cyclopentylmethylamino or cyclohexylmethylamino, or represents in each case optionally fluorine-, chlorine-, methyl-, ethyl-, n- or i-propyl-, n-, i-, s- or t-butyl-, methoxy-, ethoxy-, n- or i-propoxy-substituted phenyl, phenyloxy, phenylthio, phenylamino, benzyl, benzyloxy, benzylthio or benzylamino, or—in the case that two adjacent radicals $R^5$ and $R^5$ are located at a double bond—together with the adjacent radical $R^5$ also represents a benzo grouping.

$R^6$ preferably represents hydrogen, hydroxyl, amino, represents in each case optionally fluorine- and/or chlorine-, methoxy- or ethoxy-substituted methyl, ethyl, n- or i-propyl, n-, i- or s-butyl, methoxy, ethoxy, n- or i-propoxy, methylamino, ethylamino or dimethylamino, represents in each case optionally fluorine- and/or chlorine-substituted ethenyl, propenyl, ethinyl, propinyl or propenyloxy, represented in each case optionally fluorine- and/or chlorine-substituted cyclopropyl, cyclobutyl, cyclopentyl, cyclohexyl, cyclopropylmethyl, cyclobutylmethyl, cyclopentylmethyl or cyclohexylmethyl, or represents in each case optionally fluorine-, chlorine-, methyl-, ethyl-, n- or i-propyl-, n-, i-, s- or t-butyl-, methoxy-, ethoxy-, n- or i-propoxy-substituted phenyl or benzyl, or together with an adjacent radical $R^5$ or $R^6$ represents in each case optionally methyl- and/or ethyl-substituted propane-1,3-diyl (trimethylene), butane-1,4-diyl (tetramethylene) or pentane-1,5-diyl (pentamethylene).

A very particularly preferably represents a single bond or represents methylene.

$R^1$ very particularly preferably represents hydrogen, phenyl or in each case optionally fluorine- or chlorine-substituted methyl, ethyl, n- or i-propyl.

$R^2$ very particularly preferably represents hydrogen or in each case optionally fluorine- or chlorine-substituted methyl, ethyl, n- or i-propyl, or together with $R^1$ represents methylene or dimethylene.

$R^3$ very particularly preferably represents hydrogen, nitro, cyano, fluorine, chlorine, bromine, iodine, or represents in each case optionally fluorine-, chlorine-, methoxy- or ethoxy-substituted methyl, ethyl, n- or i-propyl, methoxy, ethoxy, methylthio, ethylthio, methylsulphinyl, ethylsulphinyl, methylsulphonyl, ethylsulphonyl, methylamino, ethylamino, dimethylamino or dimethylaminosulphonyl.

$R^4$ very particularly preferably represents hydrogen, nitro, cyano, fluorine, chlorine, bromine, iodine, or represents in each case optionally fluorine-, chlorine-, methoxy- or ethoxy-substituted methyl, ethyl, n- or i-propyl, methoxy, ethoxy, methylthio, ethylthio, methylsulphinyl, ethylsulphinyl, methylsulphonyl, ethylsulphonyl, methylamino, ethylamino, dimethylamino or dimethylaminosulphonyl.

Y very particularly preferably represents hydrogen, represents in each case optionally cyano-, fluorine-, chlorine-, bromine-, methoxy-, ethoxy-, n- or i-propoxy-substituted methyl, ethyl, n- or i-propyl, n-, i-, s- or t-butyl, represents in each case optionally fluorine-, chlorine- or bromine-substituted propenyl, butenyl, pentenyl, propinyl or butinyl, or represents in each case optionally nitro-, amino-, cyano-, fluorine-, chlorine-, bromine-, methyl-, ethyl-, n- or i-propyl-, n-, i-, s- or t-butyl-, trifluoromethyl-, methoxymethyl-, ethoxymethyl-, methoxyethyl-, ethoxyethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphinyl-, methylsulphonyl, ethylsulphonyl-, trifluoromethylsulphonyl-, acetyl-, propionyl-, methoxycarbonyl-, ethoxycarbonyl-, acetylamino-, propionylamino-, methoxycarbonylamino-, ethoxycarbonylamino-, methylsulphonylamino- or ethylsulphonylamino-substituted phenyl or benzyl.

Z very particularly preferably represents the heterocyclic groupings below

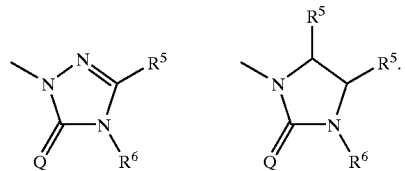

$R^5$ particularly preferably represents hydrogen, fluorine, chlorine, bromine, represents in each case optionally fluorine-, chlorine-, methoxy-, ethoxy-, n- or i-propoxy-, methylthio-, ethylthio-, methylsulphinyl-, ethylsulphinyl-, methylsulphonyl-, ethylsulphonyl-substituted methyl, ethyl, n- or i-propyl, n-, i- or s-butyl, methoxy, ethoxy, n- or i-propoxy, n-, i- or s-butoxy, methylthio, ethylthio, n- or i-propylthio, n-, i- or s-butylthio, methylsulphinyl, ethylsulphinyl, n- or i-propylsulphinyl, methylsulphonyl, ethylsulphonyl, n- or i-propylsulphonyl, represents methylamino, ethylamino, n- or i-propylamino, n-, i- or s-butylamino, dimethylamino or diethylamino, represents in each case optionally fluorine- and/or chlorine-substituted ethenyl, propenyl, butenyl, ethinyl, propinyl, butinyl, propenyloxy, butenyloxy, propenylthio or represents in each case optionally fluorine- and/or chlorine-substituted cyclopropyl, cyclopropyloxy, cyclopropylthio, cyclopropylamino, cyclopropylmethyl, cyclopropylmethoxy, cyclopropylmethylthio or cyclopropylmethylamino.

$R^6$ particularly preferably represents hydrogen, represents amino, represents in each case optionally fluorine- and/or chlorine-, methoxy- or ethoxy-substituted methyl, ethyl, methoxy, ethoxy, methylamino or ethylamino, represents dimethylamino, or represents in each case optionally fluorine- and/or chlorine-substituted cyclopropyl, cyclopropylmethyl, phenyl or benzyl, or together with an adjacent radical $R^5$ or $R^6$ represents in each case optionally methyl- and/or ethyl-substituted propane-1,3-diyl (trimethylene), butane-1, 4-diyl (tetramethylene) or pentane-1,5-diyl (pentamethylene).

A most preferably represents methylene.

$R^1$ most preferably represents hydrogen.

$R^2$ most preferably represents hydrogen.

$R^3$ most preferably represents chlorine, trifluoromethyl or methoxy.

$R^4$ most preferably represents chlorine, trifluoromethyl or methylsulphonyl.

Y most preferably represents hydrogen, represents in each case optionally fluorine-, chlorine- or methoxy-substituted methyl, ethyl, n- or i-propyl, n-, i-, s- or t-butyl, represents in each case optionally fluorine- or chlorine-substituted propenyl, butenyl, pentenyl or represents optionally amino-, cyano-, fluorine-, chlorine-, methyl-, ethyl-, trifluoromethyl-, methoxy- or ethoxy-substituted phenyl.

$R^5$ very particularly preferably represents hydrogen, methyl or ethyl.

$R^6$ very particularly preferably represents hydrogen, methyl, ethyl, n- or i-propyl, n-, i-, s- or t-butyl, cyclopropyl, cyclopropylmethyl, cyclopentyl, cyclopentylmethyl, cyclohexyl, cyclohexylmethyl, phenyl or benzyl.

$R^5$ most preferably represents hydrogen.

$R^6$ most preferably represents methyl, ethyl, n- or i-propyl, n-, i-, s- or t-butyl, cyclopropyl, cyclopropylmethyl or phenyl.

The invention preferably also provides the sodium, potassium, magnesium, calcium, ammonium, $C_1$–$C_4$-alkyl-ammonium, di-($C_1$–$C_4$-alkyl)-ammonium, tri-($C_1$–$C_4$-alkyl)-ammonium, tetra-($C_1$–$C_4$-alkyl)-ammonium, tri-($C_1$–$C_4$-alkyl)-sulphonium, $C_5$- or $C_6$-Cycloalkyl-ammonium and di-($C_1$–$C_2$-alkyl)-benzyl-ammonium salts of compounds of the formula (I), in which A, n, $R^1$, $R^2$, $R^3$, $R^4$, Y and Z are each as defined above, or else complex compounds (coordination compounds) of these compounds with metals such as copper, iron, cobalt, nickel.

Preference according to the invention is given to compounds of the formula (I) which contain a combination of the meanings mentioned above as being preferred.

Particular preference according to the invention is given to compounds of the formula (I) which contain a combination of the meanings listed above as being particularly preferred.

Very particular preference according to the invention is given to compounds of the formula (I) which contain a combination of the meanings listed above as being very particularly preferred.

Most preference according to the invention is given to compounds of the formula (I) which contain a combination of the meanings listed above as being most preferred.

The general or preferred radical definitions listed above apply both to the end products of the formula (I) and, correspondingly, to the starting materials or intermediates required in each case for the preparation. These radical definitions can be combined with one another as desired, i.e. including combinations between the given preferred ranges.

The position of the radicals $R^1$, $R^2$, $R^3$, $R^4$ and A-Z can vary according to formula (I).

The radical $R^3$ is preferably in position (4) on the phenyl ring, particularly preferably in position (2).

The radical $R^4$ is preferably in position (4) on the phenyl ring, if the radical $R^3$ is in position (2).

The radical A-Z is preferably in position (2) on the phenyl ring, particularly preferably in position (3), and particular preference is given to the substitution pattern (2)-$R^3$, (4)-$R^4$ and (3)-A-Z.

The present invention provides in particular the compounds of the general formulae (IA), (IB) and (IC) below.

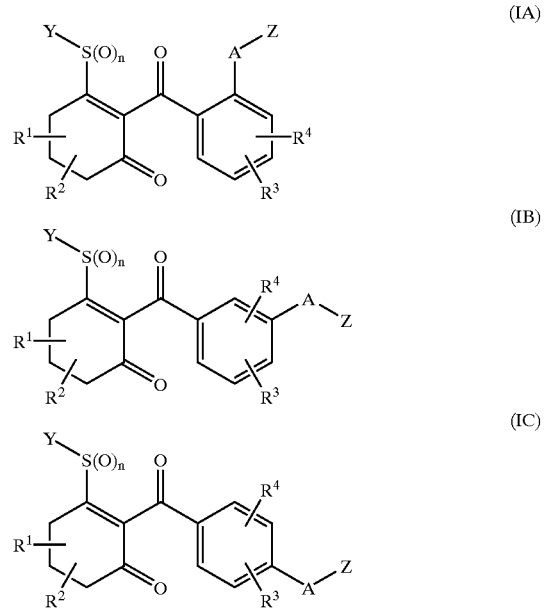

In the general formulae (IA), (IB) and (IC), n, A, $R^1$, $R^2$, $R^3$, $R^4$, Y and Z have in each case the meanings given in the definitions above.

Very particular emphasis is given to the compounds of the general formulae (IA), (IB) and (IC) in which A represents methylene.

Examples of compounds of the general formula (I) according to the invention are listed in the groups below.

Group 1

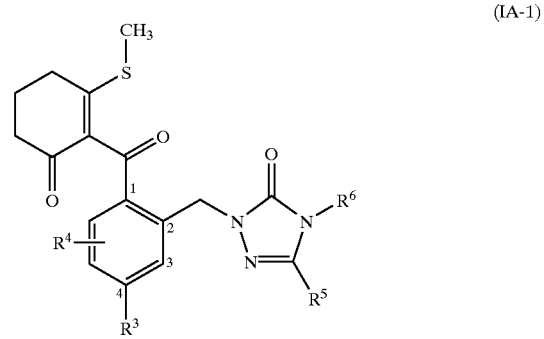

Here, $R^3$, $R^4$, $R^5$ and $R^6$ each have, for example, the meanings given in the table below:

| $R^3$ | (position) $R^4$ | $R^5$ | $R^6$ |
|---|---|---|---|
| H | — | $CF_3$ | $CH_3$ |
| F | — | $CF_3$ | $CH_3$ |
| Cl | — | $CF_3$ | $CH_3$ |
| Br | — | $CF_3$ | $CH_3$ |
| I | — | $CF_3$ | $CH_3$ |
| $NO_2$ | — | $CF_3$ | $CH_3$ |
| CN | — | $CF_3$ | $CH_3$ |
| $CH_3$ | — | $CF_3$ | $CH_3$ |
| $OCH_3$ | — | $CF_3$ | $CH_3$ |
| $CF_3$ | — | $CF_3$ | $CH_3$ |
| $OCHF_2$ | — | $CF_3$ | $CH_3$ |

-continued

| R³ | (position) R⁴ | R⁵ | R⁶ |
|---|---|---|---|
| OCF₃ | — | CF₃ | CH₃ |
| SO₂CH₃ | — | CF₃ | CH₃ |
| H | — | OCH₃ | CH₃ |
| F | — | OCH₃ | CH₃ |
| Cl | — | OCH₃ | CH₃ |
| Br | — | OCH₃ | CH₃ |
| I | — | OCH₃ | CH₃ |
| NO₂ | — | OCH₃ | CH₃ |
| CN | — | OCH₃ | CH₃ |
| CH₃ | — | OCH₃ | CH₃ |
| OCH₃ | — | OCH₃ | CH₃ |
| CF₃ | — | OCH₃ | CH₃ |
| OCHF₂ | — | OCH₃ | CH₃ |
| OCF₃ | — | OCH₃ | CH₃ |
| SO₂CH₃ | — | OCH₃ | CH₃ |
| H | — | SCH₃ | CH₃ |
| F | — | SCH₃ | CH₃ |
| Cl | — | SCH₃ | CH₃ |
| Br | — | SCH₃ | CH₃ |
| I | — | SCH₃ | CH₃ |
| NO₂ | — | SCH₃ | CH₃ |
| CN | — | SCH₃ | CH₃ |
| CH₃ | — | SCH₃ | CH₃ |
| OCH₃ | — | SCH₃ | CH₃ |
| CF₃ | — | SCH₃ | CH₃ |
| OCHF₂ | — | SCH₃ | CH₃ |
| OCF₃ | — | SCH₃ | CH₃ |
| SO₂CH₃ | — | SCH₃ | CH₃ |
| H | — | OC₂H₅ | CH₃ |
| F | — | OC₂H₅ | CH₃ |
| Cl | — | OC₂H₅ | CH₃ |
| Br | — | OC₂H₅ | CH₃ |
| I | — | OC₂H₅ | CH₃ |
| NO₂ | — | OC₂H₅ | CH₃ |
| CN | — | OC₂H₅ | CH₃ |
| CH₃ | — | OC₂H₅ | CH₃ |
| OCH₃ | — | OC₂H₅ | CH₃ |
| CF₃ | — | OC₂H₅ | CH₃ |
| OCHF₂ | — | OC₂H₅ | CH₃ |
| OCF₃ | — | OC₂H₅ | CH₃ |
| SO₂CH₃ | — | OC₂H₅ | CH₃ |
| H | — | N(CH₃)₂ | CH₃ |
| F | — | N(CH₃)₂ | CH₃ |
| Cl | — | N(CH₃)₂ | CH₃ |
| Br | — | N(CH₃)₂ | CH₃ |
| I | — | N(CH₃)₂ | CH₃ |
| NO₂ | — | N(CH₃)₂ | CH₃ |
| CN | — | N(CH₃)₂ | CH₃ |
| CH₃ | — | N(CH₃)₂ | CH₃ |
| OCH₃ | — | N(CH₃)₂ | CH₃ |
| CF₃ | — | N(CH₃)₂ | CH₃ |
| OCHF₂ | — | N(CH₃)₂ | CH₃ |
| OCF₃ | — | N(CH₃)₂ | CH₃ |
| SO₂CH₃ | — | N(CH₃)₂ | CH₃ |
| H | — | OCH₃ |  |
| F | — | OCH₃ |  |
| Cl | — | OCH₃ |  |
| Br | — | OCH₃ |  |
| I | — | OCH₃ |  |

-continued

| R³ | (position) R⁴ | R⁵ | R⁶ |
|---|---|---|---|
| NO₂ | — | OCH₃ |  |
| CN | — | OCH₃ |  |
| CH₃ | — | OCH₃ | 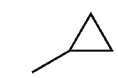 |
| OCH₃ | — | OCH₃ |  |
| CF₃ | — | OCH₃ | 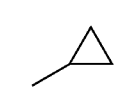 |
| OCHF₂ | — | OCH₃ |  |
| OCF₃ | — | OCH₃ |  |
| SO₂CH₃ | — | OCH₃ |  |
| H | (3-) Cl | CF₃ | CH₃ |
| F | (3-) Cl | CH₃ | CH₃ |
| Cl | (3-) Cl | OCH₃ | CH₃ |
| Br | (3-) Cl | Br | 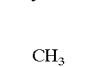 |
| Cl | (3-) Cl | CF₃ | CH₃ |
| NO₂ | (3-) Cl | CH₃ | CH₃ |
| Cl | (3-) Cl | SCH₃ | CH₃ |
| CH₃ | (3-) Cl | Cl | CH₃ |
| OCH₃ | (3-) Cl | OCH₃ | CH₃ |
| CF₃ | (3-) Cl | CF₃ | CH₃ |
| OCHF₂ | (3-) Cl | CH₃ | CH₃ |
| OCF₃ | (3-) Cl | CH₃ | CH₃ |
| SO₂CH₃ | (3-) Cl | OCH₃ | CH₃ |
| F | — | C₂H₅ | OCH₃ |
| Cl | — | C₂H₅ | OCH₃ |
| Br | — | C₂H₅ | OCH₃ |
| CF₃ | — | C₂H₅ | OCH₃ |
| SO₂CH₃ | — | C₂H₅ | OCH₃ |

-continued

| R³ | (position) R⁴ | R⁵ | R⁶ |
|---|---|---|---|
| F | — | C₂H₅ | C₂H₅ |
| Cl | — | C₂H₅ | C₂H₅ |
| Br | — | C₂H₅ | C₂H₅ |
| CF₃ | — | C₂H₅ | C₂H₅ |
| SO₂CH₃ | — | C₂H₅ | C₂H₅ |

Group 2

(IA-2)

Here, $R^3$, $R^4$, $R^5$ and $R^6$ each have, for example, the meanings given above in Group 1.

Group 3

(IA-3)

Here, $R^3$, $R^4$, $R^5$ and $R^6$ each have, for example, the meanings given above in Group 1.

Group 4

(IA-4)

Here, $R^3$, $R^4$, $R^5$ and $R^6$ each have, for example, the meanings given above in Group 1.

Group 5

(IA-5)

Here, $R^3$, $R^4$, $R^5$ and $R^6$ each have, for example, the meanings given above in Group 1.

Group 6

(IB-1)

Here, $R^3$, $R^4$, $R^5$ and $R^6$ each have, for example, the meanings given above in the table below.

| R³ | (position) R⁴ | R⁵ | R⁶ |
|---|---|---|---|
| Cl | (2-) Cl | CF₃ | CH₃ |
| Cl | (2-) Cl | SCH₃ | CH₃ |
| Cl | (2-) Cl | SC₂H₅ | CH₃ |
| Cl | (2-) Cl | SC₃H₇ | CH₃ |
| Cl | (2-) Cl | SC₃H₇-i | CH₃ |
| Cl | (2-) Cl | ⟨S-CH₂-CH=CH₂⟩ | CH₃ |
| Cl | (2-) Cl | ⟨S-CH₂-C≡CH⟩ | CH₃ |
| Cl | (2-) Cl | ⟨S-CH=CH-CH₃⟩ | CH₃ |
| Cl | (2-) Cl | ⟨S-C≡CH⟩ | CH₃ |

| R³ | (position) R⁴ | R⁵ | R⁶ |
|---|---|---|---|
| Cl | (2-) Cl | SCH₂-cyclopropyl | CH₃ |
| Cl | (2-) Cl | SCH=C=CH₂ | CH₃ |
| Cl | (2-) Cl | SCH₂CN | CH₃ |
| Cl | (2-) Cl | SCH₂CH₂CN | CH₃ |
| Cl | (2-) Cl | OCH₃ | CH₃ |
| Cl | (2-) Cl | OC₂H₅ | CH₃ |
| Cl | (2-) Cl | OC₃H₇ | CH₃ |
| Cl | (2-) Cl | OC₃H₇-i | CH₃ |
| Cl | (2-) Cl | OC₄H₉ | CH₃ |
| Cl | (2-) Cl | OCH₂CF₃ | CH₃ |
| Cl | (2-) Cl | OCH₂-cyclopropyl | CH₃ |
| Cl | (2-) Cl | OC₆H₅ | CH₃ |
| Cl | (2-) Cl | H | CH₃ |
| Cl | (2-) Cl | CH₃ | CH₃ |
| Cl | (2-) Cl | C₂H₅ | CH₃ |
| Cl | (2-) Cl | C₃H₇ | CH₃ |
| Cl | (2-) Cl | C₃H₇-i | CH₃ |
| Cl | (2-) Cl | C₄H₉ | CH₃ |
| Cl | (2-) Cl | C₄H₉-i | CH₃ |
| Cl | (2-) Cl | C₄H₉-s | CH₃ |
| Cl | (2-) Cl | C₄H₉-t | CH₃ |
| Cl | (2-) Cl | cyclopropyl | CH₃ |
| Cl | (2-) Cl | CH₂-cyclopropyl | CH₃ |
| Cl | (2-) Cl | CH=CHCH₃ | CH₃ |
| Cl | (2-) Cl | phenyl | CH₃ |
| Cl | (2-) Cl | 4-Cl-phenyl | CH₃ |
| Cl | (2-) Cl | CH₂-phenyl | CH₃ |
| Cl | (2-) Cl | N(CH₃)₂ | CH₃ |
| Cl | (2-) Cl | 4-morpholinyl | CH₃ |
| Cl | (2-) Cl | Cl | CH₃ |
| Cl | (2-) Cl | Br | CH₃ |
| SO₂CH₃ | (2-) Cl | CF₃ | CH₃ |
| SO₂CH₃ | (2-) Cl | SCH₃ | CH₃ |
| SO₂CH₃ | (2-) Cl | SC₂H₅ | CH₃ |
| SO₂CH₃ | (2-) Cl | SC₃H₇ | CH₃ |
| SO₂CH₃ | (2-) Cl | SC₃H₇-i | CH₃ |
| SO₂CH₃ | (2-) Cl | SCH₂CH=CH₂ | CH₃ |
| SO₂CH₃ | (2-) Cl | SCH₂C≡CH | CH₃ |
| SO₂CH₃ | (2-) Cl | SCH=CHCH₃ | CH₃ |
| SO₂CH₃ | (2-) Cl | SC≡CCH₃ | CH₃ |
| SO₂CH₃ | (2-) Cl | SCH₂-cyclopropyl | CH₃ |
| SO₂CH₃ | (2-) Cl | SCH=C=CH₂ | CH₃ |
| SO₂CH₃ | (2-) Cl | SCH₂CN | CH₃ |
| SO₂CH₃ | (2-) Cl | SCH₂CH₂CN | CH₃ |
| SO₂CH₃ | (2-) Cl | OCH₃ | CH₃ |
| SO₂CH₃ | (2-) Cl | OC₂H₅ | CH₃ |
| SO₂CH₃ | (2-) Cl | OC₃H₇ | CH₃ |
| SO₂CH₃ | (2-) Cl | OC₃H₇-i | CH₃ |
| SO₂CH₃ | (2-) Cl | OC₄H₉ | CH₃ |
| SO₂CH₃ | (2-) Cl | OCH₂CF₃ | CH₃ |
| SO₂CH₃ | (2-) Cl | OCH₂-cyclopropyl | CH₃ |
| SO₂CH₃ | (2-) Cl | OC₆H₅ | CH₃ |
| SO₂CH₃ | (2-) Cl | H | CH₃ |
| SO₂CH₃ | (2-) Cl | CH₃ | CH₃ |
| SO₂CH₃ | (2-) Cl | C₂H₅ | CH₃ |
| SO₂CH₃ | (2-) Cl | C₃H₇ | CH₃ |
| SO₂CH₃ | (2-) Cl | C₃H₇-i | CH₃ |
| SO₂CH₃ | (2-) Cl | C₄H₉ | CH₃ |
| SO₂CH₃ | (2-) Cl | C₄H₉-i | CH₃ |
| SO₂CH₃ | (2-) Cl | C₄H₉-s | CH₃ |
| SO₂CH₃ | (2-) Cl | C₄H₉-t | CH₃ |
| SO₂CH₃ | (2-) Cl | cyclopropyl | CH₃ |
| SO₂CH₃ | (2-) Cl | CH₂-cyclopropyl | CH₃ |

-continued

| R³ | (position) R⁴ | R⁵ | R⁶ |
|---|---|---|---|
| SO₂CH₃ | (2-) Cl | CH=CHCH₃ | CH₃ |
| SO₂CH₃ | (2-) Cl | [4-methylphenyl] | CH₃ |
| SO₂CH₃ | (2-) Cl | [4-chloro-phenyl-methyl] | CH₃ |
| SO₂CH₃ | (2-) Cl | [benzyl-CH₂] | CH₃ |
| SO₂CH₃ | (2-) Cl | N(CH₃)₂ | CH₃ |
| SO₂CH₃ | (2-) Cl | [N-methylmorpholine] | CH₃ |
| SO₂CH₃ | (2-) Cl | Cl | CH₃ |
| SO₂CH₃ | (2-) Cl | Br | CH₃ |
| Cl | (2-) SO₂CH₃ | CF₃ | CH₃ |
| Cl | (2-) SO₂CH₃ | SCH₃ | CH₃ |
| Cl | (2-) SO₂CH₃ | SC₂H₅ | CH₃ |
| Cl | (2-) SO₂CH₃ | SC₃H₇ | CH₃ |
| Cl | (2-) SO₂CH₃ | SC₃H₇-i | CH₃ |
| Cl | (2-) SO₂CH₃ | SCH₂CH=CH₂ | CH₃ |
| Cl | (2-) SO₂CH₃ | SCH₂C≡CH | CH₃ |
| Cl | (2-) SO₂CH₃ | SCH=CHCH₃ | CH₃ |
| Cl | (2-) SO₂CH₃ | SC≡CCH₃ | CH₃ |
| Cl | (2-) SO₂CH₃ | SCH₂-cyclopropyl | CH₃ |
| Cl | (2-) SO₂CH₃ | SCH=C=CH₂ | CH₃ |
| Cl | (2-) SO₂CH₃ | SCH₂CN | CH₃ |
| Cl | (2-) SO₂CH₃ | SCH₂CH₂CN | CH₃ |
| Cl | (2-) SO₂CH₃ | OCH₃ | CH₃ |
| Cl | (2-) SO₂CH₃ | OC₂H₅ | CH₃ |
| Cl | (2-) SO₂CH₃ | OC₃H₇ | CH₃ |
| Cl | (2-) SO₂CH₃ | OC₃H₇-i | CH₃ |

-continued

| R³ | (position) R⁴ | R⁵ | R⁶ |
|---|---|---|---|
| Cl | (2-) SO₂CH₃ | OC₄H₉ | CH₃ |
| Cl | (2-) SO₂CH₃ | OCH₂CF₃ | CH₃ |
| Cl | (2-) SO₂CH₃ | OCH₂-cyclopropyl | CH₃ |
| Cl | (2-) SO₂CH₃ | OC₆H₅ | CH₃ |
| Cl | (2-) SO₂CH₃ | H | CH₃ |
| Cl | (2-) SO₂CH₃ | CH₃ | CH₃ |
| Cl | (2-) SO₂CH₃ | C₂H₅ | CH₃ |
| Cl | (2-) SO₂CH₃ | C₃H₇ | CH₃ |
| Cl | (2-) SO₂CH₃ | C₃H₇-i | CH₃ |
| Cl | (2-) SO₂CH₃ | C₄H₉ | CH₃ |
| Cl | (2-) SO₂CH₃ | C₄H₉-i | CH₃ |
| Cl | (2-) SO₂CH₃ | C₄H₉-s | CH₃ |
| Cl | (2-) SO₂CH₃ | C₄H₉-t | CH₃ |
| Cl | (2-) SO₂CH₃ | cyclopropyl | CH₃ |
| Cl | (2-) SO₂CH₃ | CH₂-cyclopropyl | CH₃ |
| Cl | (2-) SO₂CH₃ | CH=CHCH₃ | CH₃ |
| Cl | (2-) SO₂CH₃ | [4-methylphenyl] | CH₃ |
| Cl | (2-) SO₂CH₃ | [4-chloro-phenyl-methyl] | CH₃ |
| Cl | (2-) SO₂CH₃ | [benzyl-CH₂] | CH₃ |
| Cl | (2-) SO₂CH₃ | N(CH₃)₂ | CH₃ |
| Cl | (2-) SO₂CH₃ | [N-methylmorpholine] | CH₃ |
| Cl | (2-) SO₂CH₃ | Cl | CH₃ |
| Cl | (2-) SO₂CH₃ | Br | CH₃ |
| Cl | (2-) Cl | CF₃ | cyclopropyl |
| Cl | (2-) Cl | SCH₃ | cyclopropyl |
| Cl | (2-) Cl | SC₂H₅ | cyclopropyl |

-continued

| R³ | (position) R⁴ | R⁵ | R⁶ |
|---|---|---|---|
| Cl | (2-) Cl | SC₃H₇ | cyclopropyl |
| Cl | (2-) Cl | SC₃H₇-i | cyclopropyl |
| Cl | (2-) Cl | CH₂=CHCH₂S– | cyclopropyl |
| Cl | (2-) Cl | HC≡CCH₂S– | cyclopropyl |
| Cl | (2-) Cl | CH₃CH=CHS– | cyclopropyl |
| Cl | (2-) Cl | CH₃C≡CS– | cyclopropyl |
| Cl | (2-) Cl | cyclopropyl-CH₂-S– | cyclopropyl |
| Cl | (2-) Cl | SCH=C=CH₂ | cyclopropyl |
| Cl | (2-) Cl | SCH₂CN | cyclopropyl |
| Cl | (2-) Cl | SCH₂CH₂CN | cyclopropyl |
| Cl | (2-) Cl | OCH₃ | cyclopropyl |
| Cl | (2-) Cl | OC₂H₅ | cyclopropyl |
| Cl | (2-) Cl | OC₃H₇ | cyclopropyl |
| Cl | (2-) Cl | OC₃H₇-i | cyclopropyl |
| Cl | (2-) Cl | OC₄H₉ | cyclopropyl |

-continued

| R³ | (position) R⁴ | R⁵ | R⁶ |
|---|---|---|---|
| Cl | (2-) Cl | OCH₂CF₃ | cyclopropyl |
| Cl | (2-) Cl | cyclopropyl-CH₂-O– | cyclopropyl |
| Cl | (2-) Cl | OC₆H₅ | cyclopropyl |
| Cl | (2-) Cl | H | cyclopropyl |
| Cl | (2-) Cl | CH₃ | cyclopropyl |
| Cl | (2-) Cl | C₂H₅ | cyclopropyl |
| Cl | (2-) Cl | C₃H₇ | cyclopropyl |
| Cl | (2-) Cl | C₃H₇-i | cyclopropyl |
| Cl | (2-) Cl | C₄H₉ | cyclopropyl |
| Cl | (2-) Cl | C₄H₉-i | cyclopropyl |
| Cl | (2-) Cl | C₄H₉-s | cyclopropyl |
| Cl | (2-) Cl | C₄H₉-t | cyclopropyl |
| Cl | (2-) Cl | cyclopropyl-CH₂– | cyclopropyl |
| Cl | (2-) Cl | cyclopropyl-CH₂CH₂– | cyclopropyl |
| Cl | (2-) Cl | CH=CHCH₃ | cyclopropyl |
| Cl | (2-) Cl | phenyl-CH₂– | cyclopropyl |

-continued

| R³ | (position) R⁴ | R⁵ | R⁶ |
|---|---|---|---|
| Cl | (2-) Cl | 4-chlorophenylmethyl | cyclopropyl |
| Cl | (2-) Cl | phenylethyl | cyclopropyl |
| Cl | (2-) Cl | N(CH₃)₂ | cyclopropyl |
| Cl | (2-) Cl | N-methylmorpholine | cyclopropyl |
| Cl | (2-) Cl | Cl | cyclopropyl |
| Cl | (2-) Cl | Br | cyclopropyl |
| SO₂CH₃ | (2-) Cl | CF₃ | cyclopropyl |
| SO₂CH₃ | (2-) Cl | SCH₃ | cyclopropyl |
| SO₂CH₃ | (2-) Cl | SC₂H₅ | cyclopropyl |
| SO₂CH₃ | (2-) Cl | SC₃H₇ | cyclopropyl |
| SO₂CH₃ | (2-) Cl | SC₃H₇-i | cyclopropyl |
| SO₂CH₃ | (2-) Cl | SCH₂CH=CH₂ | cyclopropyl |
| SO₂CH₃ | (2-) Cl | SCH₂C≡CH | cyclopropyl |
| SO₂CH₃ | (2-) Cl | SCH=CHCH₃ | cyclopropyl |
| SO₂CH₃ | (2-) Cl | SC≡CCH₃ | cyclopropyl |

-continued

| R³ | (position) R⁴ | R⁵ | R⁶ |
|---|---|---|---|
| SO₂CH₃ | (2-) Cl | S-CH₂-cyclopropyl | cyclopropyl |
| SO₂CH₃ | (2-) Cl | SCH=C=CH₂ | cyclopropyl |
| SO₂CH₃ | (2-) Cl | SCH₂CN | cyclopropyl |
| SO₂CH₃ | (2-) Cl | SCH₂CH₂CN | cyclopropyl |
| SO₂CH₃ | (2-) Cl | OCH₃ | cyclopropyl |
| SO₂CH₃ | (2-) Cl | OC₂H₅ | cyclopropyl |
| SO₂CH₃ | (2-) Cl | OC₃H₇ | cyclopropyl |
| SO₂CH₃ | (2-) Cl | OC₃H₇-i | cyclopropyl |
| SO₂CH₃ | (2-) Cl | OC₄H₉ | cyclopropyl |
| SO₂CH₃ | (2-) Cl | OCH₂CF₃ | cyclopropyl |
| SO₂CH₃ | (2-) Cl | O-CH₂-cyclopropyl | cyclopropyl |
| SO₂CH₃ | (2-) Cl | OC₆H₅ | cyclopropyl |
| SO₂CH₃ | (2-) Cl | H | cyclopropyl |
| SO₂CH₃ | (2-) Cl | CH₃ | cyclopropyl |
| SO₂CH₃ | (2-) Cl | C₂H₅ | cyclopropyl |
| SO₂CH₃ | (2-) Cl | C₃H₇ | cyclopropyl |

-continued

| R³ | (position) R⁴ | R⁵ | R⁶ |
|---|---|---|---|
| SO₂CH₃ | (2-) Cl | C₃H₇-i | cyclopropyl |
| SO₂CH₃ | (2-) Cl | C₄H₉ | cyclopropyl |
| SO₂CH₃ | (2-) Cl | C₄H₉-i | cyclopropyl |
| SO₂CH₃ | (2-) Cl | C₄H₉-s | cyclopropyl |
| SO₂CH₃ | (2-) Cl | C₄H₉-t | cyclopropyl |
| SO₂CH₃ | (2-) Cl | cyclopropyl | cyclopropyl |
| SO₂CH₃ | (2-) Cl | cyclopropylmethyl | cyclopropyl |
| SO₂CH₃ | (2-) Cl | CH=CHCH₃ | cyclopropyl |
| SO₂CH₃ | (2-) Cl | phenyl | cyclopropyl |
| SO₂CH₃ | (2-) Cl | 4-chlorophenyl | cyclopropyl |
| SO₂CH₃ | (2-) Cl | benzyl | cyclopropyl |
| SO₂CH₃ | (2-) Cl | N(CH₃)₂ | cyclopropyl |
| SO₂CH₃ | (2-) Cl | morpholino | cyclopropyl |
| SO₂CH₃ | (2-) Cl | Cl | cyclopropyl |
| SO₂CH₃ | (2-) Cl | Br | cyclopropyl |
| Cl | (2-) SO₂CH₃ | CF₃ | cyclopropyl |
| Cl | (2-) SO₂CH₃ | SCH₃ | cyclopropyl |
| Cl | (2-) SO₂CH₃ | SC₂H₅ | cyclopropyl |
| Cl | (2-) SO₂CH₃ | SC₃H₇ | cyclopropyl |
| Cl | (2-) SO₂CH₃ | SC₃H₇-i | cyclopropyl |
| Cl | (2-) SO₂CH₃ | SCH₂CH=CH₂ | cyclopropyl |
| Cl | (2-) SO₂CH₃ | SCH₂C≡CH | cyclopropyl |
| Cl | (2-) SO₂CH₃ | SCH=CHCH₃ | cyclopropyl |
| Cl | (2-) SO₂CH₃ | SC≡CCH₃ | cyclopropyl |
| Cl | (2-) SO₂CH₃ | SCH₂-cyclopropyl | cyclopropyl |
| Cl | (2-) SO₂CH₃ | SCH=C=CH₂ | cyclopropyl |
| Cl | (2-) SO₂CH₃ | SCH₂CN | cyclopropyl |
| Cl | (2-) SO₂CH₃ | SCH₂CH₂CN | cyclopropyl |
| Cl | (2-) SO₂CH₃ | OCH₃ | cyclopropyl |
| Cl | (2-) SO₂CH₃ | OC₂H₅ | cyclopropyl |
| Cl | (2-) SO₂CH₃ | OC₃H₇ | cyclopropyl |

| R³ | (position) R⁴ | R⁵ | R⁶ |
|---|---|---|---|
| Cl | (2-) SO₂CH₃ | OC₃H₇-i | cyclopropyl |
| Cl | (2-) SO₂CH₃ | OC₄H₉ | cyclopropyl |
| Cl | (2-) SO₂CH₃ | OCH₂CF₃ | cyclopropyl |
| Cl | (2-) SO₂CH₃ | cyclopropylmethoxy | cyclopropyl |
| Cl | (2-) SO₂CH₃ | OC₆H₅ | cyclopropyl |
| Cl | (2-) SO₂CH₃ | H | cyclopropyl |
| Cl | (2-) SO₂CH₃ | CH₃ | cyclopropyl |
| Cl | (2-) SO₂CH₃ | C₂H₅ | cyclopropyl |
| Cl | (2-) SO₂CH₃ | C₃H₇ | cyclopropyl |
| Cl | (2-) SO₂CH₃ | C₃H₇-i | cyclopropyl |
| Cl | (2-) SO₂CH₃ | C₄H₉ | cyclopropyl |
| Cl | (2-) SO₂CH₃ | C₄H₉-i | cyclopropyl |
| Cl | (2-) SO₂CH₃ | C₄H₉-s | cyclopropyl |
| Cl | (2-) SO₂CH₃ | C₄H₉-t | cyclopropyl |
| Cl | (2-) SO₂CH₃ | cyclopropyl | cyclopropyl |
| Cl | (2-) SO₂CH₃ | cyclopropylmethyl | cyclopropyl |
| Cl | (2-) SO₂CH₃ | CH=CHCH₃ | cyclopropyl |
| Cl | (2-) SO₂CH₃ | phenyl | cyclopropyl |
| Cl | (2-) SO₂CH₃ | 4-chlorophenyl | cyclopropyl |
| Cl | (2-) SO₂CH₃ | benzyl | cyclopropyl |
| Cl | (2-) SO₂CH₃ | N(CH₃)₂ | cyclopropyl |
| Cl | (2-) SO₂CH₃ | morpholinyl | cyclopropyl |
| Cl | (2-) SO₂CH₃ | Cl | cyclopropyl |
| Cl | (2-) SO₂CH₃ | Br | cyclopropyl |
| Cl | (2-) Cl | CF₃ | N(CH₃)₂ |
| Cl | (2-) Cl | SCH₃ | N(CH₃)₂ |
| Cl | (2-) Cl | SC₂H₅ | N(CH₃)₂ |
| Cl | (2-) Cl | SC₃H₇ | N(CH₃)₂ |
| Cl | (2-) Cl | SC₃H₇-i | N(CH₃)₂ |
| Cl | (2-) Cl | SCH₂CH=CH₂ | N(CH₃)₂ |
| Cl | (2-) Cl | SCH₂C≡CH | N(CH₃)₂ |
| Cl | (2-) Cl | SCH=CHCH₃ | N(CH₃)₂ |
| Cl | (2-) Cl | SC≡CCH₃ | N(CH₃)₂ |

-continued

| R³ | (position) R⁴ | R⁵ | R⁶ |
|---|---|---|---|
| Cl | (2-) Cl | cyclopropylmethylthio (-CH₂-S-cyclopropyl) | N(CH₃)₂ |
| Cl | (2-) Cl | SCH=C=CH₂ | N(CH₃)₂ |
| Cl | (2-) Cl | SCH₂CN | N(CH₃)₂ |
| Cl | (2-) Cl | SCH₂CH₂CN | N(CH₃)₂ |
| Cl | (2-) Cl | OCH₃ | N(CH₃)₂ |
| Cl | (2-) Cl | OC₂H₅ | N(CH₃)₂ |
| Cl | (2-) Cl | OC₃H₇ | N(CH₃)₂ |
| Cl | (2-) Cl | OC₃H₇-i | N(CH₃)₂ |
| Cl | (2-) Cl | OC₄H₉ | N(CH₃)₂ |
| Cl | (2-) Cl | OCH₂CF₃ | N(CH₃)₂ |
| Cl | (2-) Cl | cyclopropylmethoxy (-CH₂-O-cyclopropyl) | N(CH₃)₂ |
| Cl | (2-) Cl | OC₆H₅ | N(CH₃)₂ |
| Cl | (2-) Cl | H | N(CH₃)₂ |
| Cl | (2-) Cl | CH₃ | N(CH₃)₂ |
| Cl | (2-) Cl | C₂H₅ | N(CH₃)₂ |
| Cl | (2-) Cl | C₃H₇ | N(CH₃)₂ |
| Cl | (2-) Cl | C₃H₇-i | N(CH₃)₂ |
| Cl | (2-) Cl | C₄H₉ | N(CH₃)₂ |
| Cl | (2-) Cl | C₄H₉-i | N(CH₃)₂ |
| Cl | (2-) Cl | C₄H₉-s | N(CH₃)₂ |
| Cl | (2-) Cl | C₄H₉-t | N(CH₃)₂ |
| Cl | (2-) Cl | cyclopropyl | N(CH₃)₂ |
| Cl | (2-) Cl | cyclopropylmethyl | N(CH₃)₂ |
| Cl | (2-) Cl | CH=CHCH₃ | N(CH₃)₂ |
| Cl | (2-) Cl | 4-methylphenyl | N(CH₃)₂ |
| Cl | (2-) Cl | 4-chloro-methylphenyl | N(CH₃)₂ |
| Cl | (2-) Cl | benzyl (phenyl-CH₂-) | N(CH₃)₂ |
| Cl | (2-) Cl | N(CH₃)₂ | N(CH₃)₂ |
| Cl | (2-) Cl | N-methylmorpholinyl | N(CH₃)₂ |
| Cl | (2-) Cl | Cl | N(CH₃)₂ |
| Cl | (2-) Cl | Br | N(CH₃)₂ |
| SO₂CH₃ | (2-) Cl | CF₃ | N(CH₃)₂ |
| SO₂CH₃ | (2-) Cl | SCH₃ | N(CH₃)₂ |
| SO₂CH₃ | (2-) Cl | SC₂H₅ | N(CH₃)₂ |
| SO₂CH₃ | (2-) Cl | SC₃H₇ | N(CH₃)₂ |
| SO₂CH₃ | (2-) Cl | SC₃H₇-i | N(CH₃)₂ |
| SO₂CH₃ | (2-) Cl | SCH₂CH=CH₂ (allylthio) | N(CH₃)₂ |
| SO₂CH₃ | (2-) Cl | SCH₂C≡CH (propargylthio) | N(CH₃)₂ |
| SO₂CH₃ | (2-) Cl | SCH=CHCH₃ | N(CH₃)₂ |
| SO₂CH₃ | (2-) Cl | SC≡CCH₃ | N(CH₃)₂ |
| SO₂CH₃ | (2-) Cl | cyclopropylmethylthio (-CH₂-S-cyclopropyl) | N(CH₃)₂ |
| SO₂CH₃ | (2-) Cl | SCH=C=CH₂ | N(CH₃)₂ |
| SO₂CH₃ | (2-) Cl | SCH₂CN | N(CH₃)₂ |
| SO₂CH₃ | (2-) Cl | SCH₂CH₂CN | N(CH₃)₂ |
| SO₂CH₃ | (2-) Cl | OCH₃ | N(CH₃)₂ |
| SO₂CH₃ | (2-) Cl | OC₂H₅ | N(CH₃)₂ |
| SO₂CH₃ | (2-) Cl | OC₃H₇ | N(CH₃)₂ |
| SO₂CH₃ | (2-) Cl | OC₃H₇-i | N(CH₃)₂ |
| SO₂CH₃ | (2-) Cl | OC₄H₉ | N(CH₃)₂ |
| SO₂CH₃ | (2-) Cl | OCH₂CF₃ | N(CH₃)₂ |
| SO₂CH₃ | (2-) Cl | cyclopropylmethoxy (-CH₂-O-cyclopropyl) | N(CH₃)₂ |
| SO₂CH₃ | (2-) Cl | OC₆H₅ | N(CH₃)₂ |
| SO₂CH₃ | (2-) Cl | H | N(CH₃)₂ |
| SO₂CH₃ | (2-) Cl | CH₃ | N(CH₃)₂ |
| SO₂CH₃ | (2-) Cl | C₂H₅ | N(CH₃)₂ |
| SO₂CH₃ | (2-) Cl | C₃H₇ | N(CH₃)₂ |
| SO₂CH₃ | (2-) Cl | C₃H₇-i | N(CH₃)₂ |
| SO₂CH₃ | (2-) Cl | C₄H₉ | N(CH₃)₂ |
| SO₂CH₃ | (2-) Cl | C₄H₉-i | N(CH₃)₂ |
| SO₂CH₃ | (2-) Cl | C₄H₉-s | N(CH₃)₂ |
| SO₂CH₃ | (2-) Cl | C₄H₉-t | N(CH₃)₂ |
| SO₂CH₃ | (2-) Cl | cyclopropyl | N(CH₃)₂ |
| SO₂CH₃ | (2-) Cl | cyclopropylmethyl | N(CH₃)₂ |

-continued

| R³ | (position) R⁴ | R⁵ | R⁶ |
|---|---|---|---|
| SO₂CH₃ | (2-) Cl | CH=CHCH₃ | N(CH₃)₂ |
| SO₂CH₃ | (2-) Cl | phenyl (C₆H₅-) | N(CH₃)₂ |
| SO₂CH₃ | (2-) Cl | 4-chlorophenyl | N(CH₃)₂ |
| SO₂CH₃ | (2-) Cl | benzyl (CH₂C₆H₅) | N(CH₃)₂ |
| SO₂CH₃ | (2-) Cl | N(CH₃)₂ | N(CH₃)₂ |
| SO₂CH₃ | (2-) Cl | N-methylmorpholinyl | N(CH₃)₂ |
| SO₂CH₃ | (2-) Cl | Cl | N(CH₃)₂ |
| SO₂CH₃ | (2-) Cl | Br | N(CH₃)₂ |
| Cl | (2-) SO₂CH₃ | CF₃ | N(CH₃)₂ |
| Cl | (2-) SO₂CH₃ | SCH₃ | N(CH₃)₂ |
| Cl | (2-) SO₂CH₃ | SC₂H₅ | N(CH₃)₂ |
| Cl | (2-) SO₂CH₃ | SC₃H₇ | N(CH₃)₂ |
| Cl | (2-) SO₂CH₃ | SC₃H₇-i | N(CH₃)₂ |
| Cl | (2-) SO₂CH₃ | SCH₂CH=CH₂ | N(CH₃)₂ |
| Cl | (2-) SO₂CH₃ | SCH₂C≡CH | N(CH₃)₂ |
| Cl | (2-) SO₂CH₃ | SCH=CHCH₃ | N(CH₃)₂ |
| Cl | (2-) SO₂CH₃ | SC≡CCH₃ | N(CH₃)₂ |
| Cl | (2-) SO₂CH₃ | S-cyclopropyl | N(CH₃)₂ |
| Cl | (2-) SO₂CH₃ | SCH₂-cyclopropyl | N(CH₃)₂ |
| Cl | (2-) SO₂CH₃ | SCH=C=CH₂ | N(CH₃)₂ |
| Cl | (2-) SO₂CH₃ | SCH₂CN | N(CH₃)₂ |
| Cl | (2-) SO₂CH₃ | SCH₂CH₂CN | N(CH₃)₂ |
| Cl | (2-) SO₂CH₃ | OCH₃ | N(CH₃)₂ |
| Cl | (2-) SO₂CH₃ | OC₂H₅ | N(CH₃)₂ |
| Cl | (2-) SO₂CH₃ | OC₃H₇ | N(CH₃)₂ |
| Cl | (2-) SO₂CH₃ | OC₃H₇-i | N(CH₃)₂ |
| Cl | (2-) SO₂CH₃ | OC₄H₉ | N(CH₃)₂ |
| Cl | (2-) SO₂CH₃ | OCH₂CF₃ | N(CH₃)₂ |
| Cl | (2-) SO₂CH₃ | OCH₂-cyclopropyl | N(CH₃)₂ |
| Cl | (2-) SO₂CH₃ | OC₆H₅ | N(CH₃)₂ |
| Cl | (2-) SO₂CH₃ | H | N(CH₃)₂ |
| Cl | (2-) SO₂CH₃ | CH₃ | N(CH₃)₂ |
| Cl | (2-) SO₂CH₃ | C₂H₅ | N(CH₃)₂ |
| Cl | (2-) SO₂CH₃ | C₃H₇ | N(CH₃)₂ |
| Cl | (2-) SO₂CH₃ | C₃H₇-i | N(CH₃)₂ |
| Cl | (2-) SO₂CH₃ | C₄H₉ | N(CH₃)₂ |
| Cl | (2-) SO₂CH₃ | C₄H₉-i | N(CH₃)₂ |
| Cl | (2-) SO₂CH₃ | C₄H₉-s | N(CH₃)₂ |
| Cl | (2-) SO₂CH₃ | C₄H₉-t | N(CH₃)₂ |
| Cl | (2-) SO₂CH₃ | cyclopropyl | N(CH₃)₂ |
| Cl | (2-) SO₂CH₃ | CH₂-cyclopropyl | N(CH₃)₂ |
| Cl | (2-) SO₂CH₃ | CH=CHCH₃ | N(CH₃)₂ |
| Cl | (2-) SO₂CH₃ | phenyl (C₆H₅-) | N(CH₃)₂ |
| Cl | (2-) SO₂CH₃ | 4-chlorophenyl | N(CH₃)₂ |
| Cl | (2-) SO₂CH₃ | benzyl (CH₂C₆H₅) | N(CH₃)₂ |
| Cl | (2-) SO₂CH₃ | N(CH₃)₂ | N(CH₃)₂ |
| Cl | (2-) SO₂CH₃ | N-methylmorpholinyl | N(CH₃)₂ |
| Cl | (2-) SO₂CH₃ | Cl | N(CH₃)₂ |
| Cl | (2-) SO₂CH₃ | Br | N(CH₃)₂ |
| Cl | (2-) Cl | CH₃ | OCH₃ |
| Cl | (2-) Cl | C₂H₅ | OCH₃ |
| Cl | (2-) Cl | C₃H₇ | OCH₃ |
| Cl | (2-) Cl | SCH₃ | OCH₃ |
| Cl | (2-) Cl | SC₂H₅ | OCH₃ |
| Cl | (2-) Cl | OCH₃ | OCH₃ |
| Cl | (2-) Cl | OC₂H₅ | OCH₃ |
| Cl | (2-) Cl | CH₃ | OC₂H₅ |
| Cl | (2-) Cl | C₂H₅ | OC₂H₅ |
| Cl | (2-) Cl | C₃H₇ | OC₂H₅ |
| Cl | (2-) Cl | SCH₃ | OC₂H₅ |
| Cl | (2-) Cl | SC₂H₅ | OC₂H₅ |
| Cl | (2-) Cl | OCH₃ | OC₂H₅ |
| Cl | (2-) Cl | OC₂H₅ | OC₂H₅ |
| Cl | (2-) SO₂CH₃ | CH₃ | OCH₃ |
| Cl | (2-) SO₂CH₃ | C₂H₅ | OCH₃ |

-continued

| R³ | (position) R⁴ | R⁵ | R⁶ |
|---|---|---|---|
| Cl | (2-) SO₂CH₃ | C₃H₇ | OCH₃ |
| Cl | (2-) SO₂CH₃ | SCH₃ | OCH₃ |
| Cl | (2-) SO₂CH₃ | SC₂H₅ | OCH₃ |
| Cl | (2-) SO₂CH₃ | OCH₃ | OCH₃ |
| Cl | (2-) SO₂CH₃ | OC₂H₅ | OCH₃ |
| Cl | (2-) SO₂CH₃ | CH₃ | OC₂H₅ |
| Cl | (2-) SO₂CH₃ | C₂H₅ | OC₂H₅ |
| Cl | (2-) SO₂CH₃ | C₃H₇ | OC₂H₅ |
| Cl | (2-) SO₂CH₃ | SCH₃ | OC₂H₅ |
| Cl | (2-) SO₂CH₃ | SC₂H₅ | OC₂H₅ |
| Cl | (2-) SO₂CH₃ | OCH₃ | OC₂H₅ |
| Cl | (2-) SO₂CH₃ | OC₂H₅ | OC₂H₅ |
| SO₂CH₃ | (2-) Cl | Cl | OCH₃ |
| SO₂CH₃ | (2-) Cl | Br | OCH₃ |
| SO₂CH₃ | (2-) Cl | CH₃ | OCH₃ |
| SO₂CH₃ | (2-) Cl | C₂H₅ | OCH₃ |
| SO₂CH₃ | (2-) Cl | C₃H₇ | OCH₃ |
| SO₂CH₃ | (2-) Cl | SCH₃ | OCH₃ |
| SO₂CH₃ | (2-) Cl | SC₂H₅ | OCH₃ |
| SO₂CH₃ | (2-) Cl | OCH₃ | OC₂H₅ |
| SO₂CH₃ | (2-) Cl | OC₂H₅ | OC₂H₅ |
| SO₂CH₃ | (2-) Cl | CH₃ | OC₂H₅ |
| SO₂CH₃ | (2-) Cl | C₂H₅ | OC₂H₅ |
| SO₂CH₃ | (2-) Cl | C₃H₇ | OC₂H₅ |
| SO₂CH₃ | (2-) Cl | SCH₃ | OC₂H₅ |
| SO₂CH₃ | (2-) Cl | SC₂H₅ | OC₂H₅ |
| SO₂CH₃ | (2-) Cl | OCH₃ | OC₂H₅ |
| CF₃ | (2-) Cl | Br | CH₃ |
| CF₃ | (2-) Cl | SCH₃ | CH₃ |
| CF₃ | (2-) Cl | OCH₃ | CH₃ |
| CF₃ | (2-) Cl | N(CH₃)₂ | CH₃ |
| CF₃ | (2-) Cl | CF₃ | CH₃ |
| CF₃ | (2-) NO₂ | Br | CH₃ |
| CF₃ | (2-) NO₂ | SCH₃ | CH₃ |
| CF₃ | (2-) NO₂ | OCH₃ | CH₃ |
| CF₃ | (2-) NO₂ | N(CH₃)₂ | CH₃ |
| CF₃ | (2-) NO₂ | CF₃ | CH₃ |
| CF₃ | (2-) CH₃ | Br | CH₃ |
| CF₃ | (2-) CH₃ | SCH₃ | CH₃ |
| CF₃ | (2-) CH₃ | OCH₃ | CH₃ |
| CF₃ | (2-) CH₃ | N(CH₃)₂ | CH₃ |
| CF₃ | (2-) CH₃ | CF₃ | CH₃ |
| CF₃ | (2-) OCH₃ | Br | CH₃ |
| CF₃ | (2-) OCH₃ | SCH₃ | CH₃ |
| CF₃ | (2-) OCH₃ | OCH₃ | CH₃ |
| CF₃ | (2-) OCH₃ | N(CH₃)₂ | CH₃ |
| CF₃ | (2-) OCH₃ | CF₃ | CH₃ |
| SO₂CH₃ | (2-) NO₂ | Br | CH₃ |
| SO₂CH₃ | (2-) NO₂ | SCH₃ | CH₃ |
| SO₂CH₃ | (2-) NO₂ | OCH₃ | CH₃ |
| SO₂CH₃ | (2-) NO₂ | N(CH₃)₂ | CH₃ |
| SO₂CH₃ | (2-) NO₂ | CF₃ | CH₃ |
| SO₂CH₃ | (2-) CF₃ | Br | CH₃ |
| SO₂CH₃ | (2-) CF₃ | SCH₃ | CH₃ |
| SO₂CH₃ | (2-) CF₃ | OCH₃ | CH₃ |
| SO₂CH₃ | (2-) CF₃ | N(CH₃)₂ | CH₃ |
| SO₂CH₃ | (2-) CF₃ | CF₃ | CH₃ |
| SO₂CH₃ | (2-) SO₂CH₃ | Br | CH₃ |
| SO₂CH₃ | (2-) SO₂CH₃ | SCH₃ | CH₃ |
| SO₂CH₃ | (2-) SO₂CH₃ | OCH₃ | CH₃ |
| SO₂CH₃ | (2-) SO₂CH₃ | N(CH₃)₂ | CH₃ |
| SO₂CH₃ | (2-) SO₂CH₃ | CF₃ | CH₃ |
| CN | (2-) Cl | Br | CH₃ |
| CN | (2-) Cl | SCH₃ | CH₃ |
| CN | (2-) Cl | OCH₃ | CH₃ |
| CN | (2-) Cl | N(CH₃)₂ | CH₃ |
| CN | (2-) Cl | CF₃ | CH₃ |
| CN | (2-) NO₂ | Br | CH₃ |
| CN | (2-) NO₂ | SCH₃ | CH₃ |
| CN | (2-) NO₂ | OCH₃ | CH₃ |
| CN | (2-) NO₂ | N(CH₃)₂ | CH₃ |
| CN | (2-) NO₂ | CF₃ | CH₃ |
| CN | (2-) CF₃ | Br | CH₃ |
| CN | (2-) CF₃ | SCH₃ | CH₃ |
| CN | (2-) CF₃ | OCH₃ | CH₃ |
| CN | (2-) CF₃ | N(CH₃)₂ | CH₃ |
| CN | (2-) CF₃ | CF₃ | CH₃ |
| CN | (2-) SO₂CH₃ | Br | CH₃ |
| CN | (2-) SO₂CH₃ | SCH₃ | CH₃ |
| CN | (2-) SO₂CH₃ | OCH₃ | CH₃ |
| CN | (2-) SO₂CH₃ | N(CH₃)₂ | CH₃ |
| CN | (2-) SO₂CH₃ | CF₃ | CH₃ |
| Br | (2-) NO₂ | Br | CH₃ |
| Br | (2-) NO₂ | SCH₃ | CH₃ |
| Br | (2-) NO₂ | OCH₃ | CH₃ |
| Br | (2-) NO₂ | N(CH₃)₂ | CH₃ |
| Br | (2-) NO₂ | CF₃ | CH₃ |
| Br | (2-) CF₃ | Br | CH₃ |
| Br | (2-) CF₃ | SCH₃ | CH₃ |
| Br | (2-) CF₃ | OCH₃ | CH₃ |
| Br | (2-) CF₃ | N(CH₃)₂ | CH₃ |
| Br | (2-) CF₃ | CF₃ | CH₃ |
| Br | (2-) SO₂CH₃ | Br | CH₃ |
| Br | (2-) SO₂CH₃ | SCH₃ | CH₃ |
| Br | (2-) SO₂CH₃ | OCH₃ | CH₃ |
| Br | (2-) SO₂CH₃ | N(CH₃)₂ | CH₃ |
| Br | (2-) SO₂CH₃ | CF₃ | CH₃ |
| Br | (2-) CH₃ | Br | CH₃ |
| Br | (2-) CH₃ | SCH₃ | CH₃ |
| Br | (2-) CH₃ | OCH₃ | CH₃ |
| Br | (2-) CH₃ | N(CH₃)₂ | CH₃ |
| Br | (2-) CH₃ | CF₃ | CH₃ |
| Cl | (2-) OCH₃ | CF₃ | CH₃ |
| Cl | (2-) OCH₃ | SCH₃ | CH₃ |
| Cl | (2-) OCH₃ | SC₂H₅ | CH₃ |
| Cl | (2-) OCH₃ | SC₃H₇ | CH₃ |
| Cl | (2-) OCH₃ | SC₃H₇-i | CH₃ |
| Cl | (2-) OCH₃ | 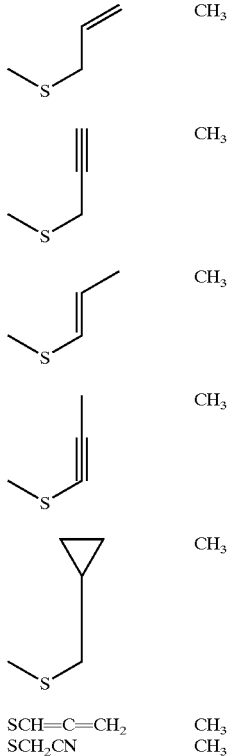 | CH₃ |
| Cl | (2-) OCH₃ | | CH₃ |
| Cl | (2-) OCH₃ | | CH₃ |
| Cl | (2-) OCH₃ | | CH₃ |
| Cl | (2-) OCH₃ | | CH₃ |
| Cl | (2-) OCH₃ | SCH=C=CH₂ | CH₃ |
| Cl | (2-) OCH₃ | SCH₂CN | CH₃ |
| Cl | (2-) OCH₃ | SCH₂CH₂CN | CH₃ |
| Cl | (2-) OCH₃ | OCH₃ | CH₃ |
| Cl | (2-) OCH₃ | OC₂H₅ | CH₃ |
| Cl | (2-) OCH₃ | OC₃H₇ | CH₃ |
| Cl | (2-) OCH₃ | OC₃H₇-i | CH₃ |
| Cl | (2-) OCH₃ | OC₄H₉ | CH₃ |
| Cl | (2-) OCH₃ | OCH₂CF₃ | CH₃ |

-continued

| R³ | (position) R⁴ | R⁵ | R⁶ |
|---|---|---|---|
| Cl | (2-) OCH₃ | (cyclopropylmethoxymethyl group) | CH₃ |
| Cl | (2-) OCH₃ | OC₆H₅ | CH₃ |
| Cl | (2-) OCH₃ | H | CH₃ |
| Cl | (2-) OCH₃ | CH₃ | CH₃ |
| Cl | (2-) OCH₃ | C₂H₅ | CH₃ |
| Cl | (2-) OCH₃ | C₃H₇ | CH₃ |
| Cl | (2-) OCH₃ | C₃H₇-i | CH₃ |
| Cl | (2-) OCH₃ | C₄H₉ | CH₃ |
| Cl | (2-) OCH₃ | C₄H₉-i | CH₃ |
| Cl | (2-) OCH₃ | C₄H₉-s | CH₃ |
| Cl | (2-) OCH₃ | C₄H₉-t | CH₃ |
| Cl | (2-) OCH₃ | (cyclopropylmethyl) | CH₃ |
| Cl | (2-) OCH₃ | (cyclopropylethyl) | CH₃ |
| Cl | (2-) OCH₃ | CH=CHCH₃ | CH₃ |
| Cl | (2-) OCH₃ | (phenylmethyl) | CH₃ |
| Cl | (2-) OCH₃ | (4-chlorophenylmethyl) | CH₃ |
| Cl | (2-) OCH₃ | (phenylethyl) | CH₃ |
| Cl | (2-) OCH₃ | N(CH₃)₂ | CH₃ |
| Cl | (2-) OCH₃ | (morpholinylmethyl) | CH₃ |
| Cl | (2-) OCH₃ | Cl | CH₃ |
| Cl | (2-) OCH₃ | Br | CH₃ |
| SO₂CH₃ | (2-) OCH₃ | CF₃ | CH₃ |
| SO₂CH₃ | (2-) OCH₃ | SCH₃ | CH₃ |
| SO₂CH₃ | (2-) OCH₃ | SC₂H₅ | CH₃ |
| SO₂CH₃ | (2-) OCH₃ | SC₃H₇ | CH₃ |
| SO₂CH₃ | (2-) OCH₃ | SC₃H₇-i | CH₃ |
| SO₂CH₃ | (2-) OCH₃ | (SCH₂CH=CH₂) | CH₃ |
| SO₂CH₃ | (2-) OCH₃ | (SCH₂C≡CH) | CH₃ |
| SO₂CH₃ | (2-) OCH₃ | (SCH=CHCH₃) | CH₃ |
| SO₂CH₃ | (2-) OCH₃ | (SC(=CH₂)CH₃) | CH₃ |
| SO₂CH₃ | (2-) OCH₃ | (S-cyclopropylmethyl) | CH₃ |
| SO₂CH₃ | (2-) OCH₃ | SCH=C=CH₂ | CH₃ |
| SO₂CH₃ | (2-) OCH₃ | SCH₂CN | CH₃ |
| SO₂CH₃ | (2-) OCH₃ | SCH₂CH₂CN | CH₃ |
| SO₂CH₃ | (2-) OCH₃ | OCH₃ | CH₃ |
| SO₂CH₃ | (2-) OCH₃ | OC₂H₅ | CH₃ |
| SO₂CH₃ | (2-) OCH₃ | OC₃H₇ | CH₃ |
| SO₂CH₃ | (2-) OCH₃ | OC₃H₇-i | CH₃ |
| SO₂CH₃ | (2-) OCH₃ | OC₄H₉ | CH₃ |
| SO₂CH₃ | (2-) OCH₃ | OCH₂CF₃ | CH₃ |
| SO₂CH₃ | (2-) OCH₃ | (cyclopropylmethoxymethyl) | CH₃ |
| SO₂CH₃ | (2-) OCH₃ | OC₆H₅ | CH₃ |
| SO₂CH₃ | (2-) OCH₃ | H | CH₃ |
| SO₂CH₃ | (2-) OCH₃ | CH₃ | CH₃ |
| SO₂CH₃ | (2-) OCH₃ | C₂H₅ | CH₃ |
| SO₂CH₃ | (2-) OCH₃ | C₃H₇ | CH₃ |
| SO₂CH₃ | (2-) OCH₃ | C₃H₇-i | CH₃ |
| SO₂CH₃ | (2-) OCH₃ | C₄H₉ | CH₃ |
| SO₂CH₃ | (2-) OCH₃ | C₄H₉-i | CH₃ |
| SO₂CH₃ | (2-) OCH₃ | C₄H₉-s | CH₃ |
| SO₂CH₃ | (2-) OCH₃ | C₄H₉-t | CH₃ |
| SO₂CH₃ | (2-) OCH₃ | (cyclopropylmethyl) | CH₃ |
| SO₂CH₃ | (2-) OCH₃ | (cyclopropylethyl) | CH₃ |
| SO₂CH₃ | (2-) OCH₃ | CH=CHCH₃ | CH₃ |
| SO₂CH₃ | (2-) OCH₃ | (phenylmethyl) | CH₃ |
| SO₂CH₃ | (2-) OCH₃ | (4-chlorophenylmethyl) | CH₃ |

| R³ | (position) R⁴ | R⁵ | R⁶ |
|---|---|---|---|
| SO₂CH₃ | (2-) OCH₃ |  | CH₃ |
| SO₂CH₃ | (2-) OCH₃ | N(CH₃)₂ | CH₃ |
| SO₂CH₃ | (2-) OCH₃ |  | CH₃ |
| SO₂CH₃ | (2-) OCH₃ | Cl | CH₃ |
| SO₂CH₃ | (2-) OCH₃ | Br | CH₃ |
| Cl | (2-) OCH₃ | CF₃ |  |
| Cl | (2-) OCH₃ | SCH₃ |  |
| Cl | (2-) OCH₃ | SC₂H₅ |  |
| Cl | (2-) OCH₃ | SC₃H₇ |  |
| Cl | (2-) OCH₃ | SC₃H₇-i |  |
| Cl | (2-) OCH₃ |  |  |
| Cl | (2-) OCH₃ |  |  |
| Cl | (2-) OCH₃ |  |  |
| Cl | (2-) OCH₃ |  | (cont.) |
| Cl | (2-) OCH₃ | (cont.) | (cont.) |
| Cl | (2-) OCH₃ | SCH=C=CH₂ | (cont.) |

| R³ | (position) R⁴ | R⁵ | R⁶ |
|---|---|---|---|
| Cl | (2-) OCH₃ | SCH₂CN | (cyclopropyl) |
| Cl | (2-) OCH₃ | SCH₂CH₂CN | (cyclopropyl) |
| Cl | (2-) OCH₃ | OCH₃ | (cyclopropyl) |
| Cl | (2-) OCH₃ | OC₂H₅ | (cyclopropyl) |
| Cl | (2-) OCH₃ | OC₃H₇ | (cyclopropyl) |
| Cl | (2-) OCH₃ | OC₃H₇-i | (cyclopropyl) |
| Cl | (2-) OCH₃ | OC₄H₉ | (cyclopropyl) |
| Cl | (2-) OCH₃ | OCH₂CF₃ | (cyclopropyl) |
| Cl | (2-) OCH₃ | (cyclopropylmethoxy) | (cyclopropyl) |
| Cl | (2-) OCH₃ | OC₆H₅ | (cyclopropyl) |
| Cl | (2-) OCH₃ | H | (cyclopropyl) |
| Cl | (2-) OCH₃ | CH₃ | (cyclopropyl) |
| Cl | (2-) OCH₃ | C₂H₅ | (cyclopropyl) |
| Cl | (2-) OCH₃ | C₃H₇ | (cyclopropyl) |
| Cl | (2-) OCH₃ | C₃H₇-i | (cyclopropyl) |
| Cl | (2-) OCH₃ | C₄H₉ | (cyclopropyl) |
| Cl | (2-) OCH₃ | C₄H₉-i | (cyclopropyl) |

| R³ | (position) R⁴ | R⁵ | R⁶ |
|---|---|---|---|
| Cl | (2-) OCH₃ | C₄H₉-s |  |
| Cl | (2-) OCH₃ | C₄H₉-t |  |
| Cl | (2-) OCH₃ |  |  |
| Cl | (2-) OCH₃ |  |  |
| Cl | (2-) OCH₃ | CH=CHCH₃ |  |
| Cl | (2-) OCH₃ |  |  |
| Cl | (2-) OCH₃ |  |  |
| Cl | (2-) OCH₃ |  |  |
| Cl | (2-) OCH₃ | N(CH₃)₂ |  |
| Cl | (2-) OCH₃ |  |  |
| Cl | (2-) OCH₃ | Cl |  |
| Cl | (2-) OCH₃ | Br |  |
| SO₂CH₃ | (2-) OCH₃ | CF₃ |  |
| SO₂CH₃ | (2-) OCH₃ | SCH₃ |  |
| SO₂CH₃ | (2-) OCH₃ | SC₂H₅ |  |
| SO₂CH₃ | (2-) OCH₃ | SC₃H₇ |  |
| SO₂CH₃ | (2-) OCH₃ | SC₃H₇-i |  |
| SO₂CH₃ | (2-) OCH₃ |  |  |
| SO₂CH₃ | (2-) OCH₃ |  |  |
| SO₂CH₃ | (2-) OCH₃ |  |  |
| SO₂CH₃ | (2-) OCH₃ |  |  |
| SO₂CH₃ | (2-) OCH₃ |  |  |
| SO₂CH₃ | (2-) OCH₃ | SCH=C=CH₂ |  |
| SO₂CH₃ | (2-) OCH₃ | SCH₂CN |  |
| SO₂CH₃ | (2-) OCH₃ | SCH₂CH₂CN |  |
| SO₂CH₃ | (2-) OCH₃ | OCH₃ |  |
| SO₂CH₃ | (2-) OCH₃ | OC₂H₅ |  |
| SO₂CH₃ | (2-) OCH₃ | OC₃H₇ |  |
| SO₂CH₃ | (2-) OCH₃ | OC₃H₇-i |  |
| SO₂CH₃ | (2-) OCH₃ | OC₄H₉ |  |
| SO₂CH₃ | (2-) OCH₃ | OCH₂CF₃ |  |

-continued

| R³ | (position) R⁴ | R⁵ | R⁶ |
|---|---|---|---|
| SO₂CH₃ | (2-) OCH₃ | CH₂-O-CH₃ (cyclopropylmethoxymethyl) | cyclopropyl |
| SO₂CH₃ | (2-) OCH₃ | OC₆H₅ | cyclopropyl |
| SO₂CH₃ | (2-) OCH₃ | H | cyclopropyl |
| SO₂CH₃ | (2-) OCH₃ | CH₃ | cyclopropyl |
| SO₂CH₃ | (2-) OCH₃ | C₂H₅ | cyclopropyl |
| SO₂CH₃ | (2-) OCH₃ | C₃H₇ | cyclopropyl |
| SO₂CH₃ | (2-) OCH₃ | C₃H₇-i | cyclopropyl |
| SO₂CH₃ | (2-) OCH₃ | C₄H₉ | cyclopropyl |
| SO₂CH₃ | (2-) OCH₃ | C₄H₉-i | cyclopropyl |
| SO₂CH₃ | (2-) OCH₃ | C₄H₉-s | cyclopropyl |
| SO₂CH₃ | (2-) OCH₃ | C₄H₉-t | cyclopropyl |
| SO₂CH₃ | (2-) OCH₃ | cyclopropyl | cyclopropyl |
| SO₂CH₃ | (2-) OCH₃ | cyclopropylmethyl | cyclopropyl |
| SO₂CH₃ | (2-) OCH₃ | CH=CHCH₃ | cyclopropyl |
| SO₂CH₃ | (2-) OCH₃ | 4-methylphenyl | cyclopropyl |
| SO₂CH₃ | (2-) OCH₃ | 4-chloro-methylphenyl | cyclopropyl |
| SO₂CH₃ | (2-) OCH₃ | benzyl | cyclopropyl |
| SO₂CH₃ | (2-) OCH₃ | N(CH₃)₂ | cyclopropyl |
| SO₂CH₃ | (2-) OCH₃ | 4-methylmorpholinyl | cyclopropyl |
| SO₂CH₃ | (2-) OCH₃ | Cl | cyclopropyl |
| SO₂CH₃ | (2-) OCH₃ | Br | cyclopropyl |
| Cl | (2-) OCH₃ | CF₃ | N(CH₃)₂ |
| Cl | (2-) OCH₃ | SCH₃ | N(CH₃)₂ |
| Cl | (2-) OCH₃ | SC₂H₅ | N(CH₃)₂ |
| Cl | (2-) OCH₃ | SC₃H₇ | N(CH₃)₂ |
| Cl | (2-) OCH₃ | SC₃H₇-i | N(CH₃)₂ |
| Cl | (2-) OCH₃ | SCH₂CH=CH₂ | N(CH₃)₂ |
| Cl | (2-) OCH₃ | SCH₂C≡CH | N(CH₃)₂ |
| Cl | (2-) OCH₃ | SCH=CHCH₃ | N(CH₃)₂ |
| Cl | (2-) OCH₃ | SCH=C=CH₂ | N(CH₃)₂ |
| Cl | (2-) OCH₃ | SCH₂-cyclopropyl | N(CH₃)₂ |
| Cl | (2-) OCH₃ | SCH=C=CH₂ | N(CH₃)₂ |
| Cl | (2-) OCH₃ | SCH₂CN | N(CH₃)₂ |
| Cl | (2-) OCH₃ | SCH₂CH₂CN | N(CH₃)₂ |
| Cl | (2-) OCH₃ | OCH₃ | N(CH₃)₂ |
| Cl | (2-) OCH₃ | OC₂H₅ | N(CH₃)₂ |
| Cl | (2-) OCH₃ | OC₃H₇ | N(CH₃)₂ |
| Cl | (2-) OCH₃ | OC₃H₇-i | N(CH₃)₂ |
| Cl | (2-) OCH₃ | OC₄H₉ | N(CH₃)₂ |
| Cl | (2-) OCH₃ | OCH₂CF₃ | N(CH₃)₂ |

-continued

| R³ | (position) R⁴ | R⁵ | R⁶ |
|---|---|---|---|
| Cl | (2-) OCH₃ | cyclopropyl | N(CH₃)₂ |
| Cl | (2-) OCH₃ | OC₆H₅ | N(CH₃)₂ |
| Cl | (2-) OCH₃ | H | N(CH₃)₂ |
| Cl | (2-) OCH₃ | CH₃ | N(CH₃)₂ |
| Cl | (2-) OCH₃ | C₂H₅ | N(CH₃)₂ |
| Cl | (2-) OCH₃ | C₃H₇ | N(CH₃)₂ |
| Cl | (2-) OCH₃ | C₃H₇-i | N(CH₃)₂ |
| Cl | (2-) OCH₃ | C₄H₉ | N(CH₃)₂ |
| Cl | (2-) OCH₃ | C₄H₉-i | N(CH₃)₂ |
| Cl | (2-) OCH₃ | C₄H₉-s | N(CH₃)₂ |
| Cl | (2-) OCH₃ | C₄H₉-t | N(CH₃)₂ |
| Cl | (2-) OCH₃ | cyclopropylmethyl | N(CH₃)₂ |
| Cl | (2-) OCH₃ | cyclopropylethyl | N(CH₃)₂ |
| Cl | (2-) OCH₃ | CH=CHCH₃ | N(CH₃)₂ |
| Cl | (2-) OCH₃ | phenyl | N(CH₃)₂ |
| Cl | (2-) OCH₃ | 4-chlorophenyl | N(CH₃)₂ |
| Cl | (2-) OCH₃ | benzyl | N(CH₃)₂ |
| Cl | (2-) OCH₃ | N(CH₃)₂ | N(CH₃)₂ |
| Cl | (2-) OCH₃ | morpholinyl | N(CH₃)₂ |
| Cl | (2-) OCH₃ | Cl | N(CH₃)₂ |
| Cl | (2-) OCH₃ | Br | N(CH₃)₂ |
| SO₂CH₃ | (2-) OCH₃ | CF₃ | N(CH₃)₂ |
| SO₂CH₃ | (2-) OCH₃ | SCH₃ | N(CH₃)₂ |
| SO₂CH₃ | (2-) OCH₃ | SC₂H₅ | N(CH₃)₂ |
| SO₂CH₃ | (2-) OCH₃ | SC₃H₇ | N(CH₃)₂ |
| SO₂CH₃ | (2-) OCH₃ | SC₃H₇-i | N(CH₃)₂ |
| SO₂CH₃ | (2-) OCH₃ | SCH₂CH=CH₂ | N(CH₃)₂ |
| SO₂CH₃ | (2-) OCH₃ | SCH₂C≡CH | N(CH₃)₂ |
| SO₂CH₃ | (2-) OCH₃ | SCH=CHCH₃ | N(CH₃)₂ |
| SO₂CH₃ | (2-) OCH₃ | SC≡CCH₃ | N(CH₃)₂ |
| SO₂CH₃ | (2-) OCH₃ | S-cyclopropylmethyl | N(CH₃)₂ |
| SO₂CH₃ | (2-) OCH₃ | SCH=C=CH₂ | N(CH₃)₂ |
| SO₂CH₃ | (2-) OCH₃ | SCH₂CN | N(CH₃)₂ |
| SO₂CH₃ | (2-) OCH₃ | SCH₂CH₂CN | N(CH₃)₂ |
| SO₂CH₃ | (2-) OCH₃ | OCH₃ | N(CH₃)₂ |
| SO₂CH₃ | (2-) OCH₃ | OC₂H₅ | N(CH₃)₂ |
| SO₂CH₃ | (2-) OCH₃ | OC₃H₇ | N(CH₃)₂ |
| SO₂CH₃ | (2-) OCH₃ | OC₃H₇-i | N(CH₃)₂ |
| SO₂CH₃ | (2-) OCH₃ | OC₄H₉ | N(CH₃)₂ |
| SO₂CH₃ | (2-) OCH₃ | OCH₂CF₃ | N(CH₃)₂ |
| SO₂CH₃ | (2-) OCH₃ | cyclopropylmethoxy | N(CH₃)₂ |
| SO₂CH₃ | (2-) OCH₃ | OC₆H₅ | N(CH₃)₂ |
| SO₂CH₃ | (2-) OCH₃ | H | N(CH₃)₂ |
| SO₂CH₃ | (2-) OCH₃ | CH₃ | N(CH₃)₂ |
| SO₂CH₃ | (2-) OCH₃ | C₂H₅ | N(CH₃)₂ |
| SO₂CH₃ | (2-) OCH₃ | C₃H₇ | N(CH₃)₂ |
| SO₂CH₃ | (2-) OCH₃ | C₃H₇-i | N(CH₃)₂ |
| SO₂CH₃ | (2-) OCH₃ | C₄H₉ | N(CH₃)₂ |
| SO₂CH₃ | (2-) OCH₃ | C₄H₉-i | N(CH₃)₂ |
| SO₂CH₃ | (2-) OCH₃ | C₄H₉-s | N(CH₃)₂ |
| SO₂CH₃ | (2-) OCH₃ | C₄H₉-t | N(CH₃)₂ |
| SO₂CH₃ | (2-) OCH₃ | cyclopropylmethyl | N(CH₃)₂ |
| SO₂CH₃ | (2-) OCH₃ | cyclopropylethyl | N(CH₃)₂ |
| SO₂CH₃ | (2-) OCH₃ | CH=CHCH₃ | N(CH₃)₂ |
| SO₂CH₃ | (2-) OCH₃ | phenyl | N(CH₃)₂ |
| SO₂CH₃ | (2-) OCH₃ | 4-chlorophenyl | N(CH₃)₂ |

-continued

| R³ | (position) R⁴ | R⁵ | R⁶ |
|---|---|---|---|
| SO₂CH₃ | (2-) OCH₃ | 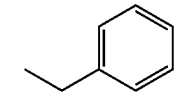 | N(CH₃)₂ |
| SO₂CH₃ | (2-) OCH₃ | N(CH₃)₂ | N(CH₃)₂ |
| SO₂CH₃ | (2-) OCH₃ | 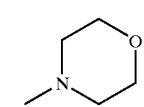 | N(CH₃)₂ |
| SO₂CH₃ | (2-) OCH₃ | Cl | N(CH₃)₂ |
| SO₂CH₃ | (2-) OCH₃ | Br | N(CH₃)₂ |
| Cl | (2-) OCH₃ | CH₃ | OCH₃ |
| Cl | (2-) OCH₃ | C₂H₅ | OCH₃ |
| Cl | (2-) OCH₃ | C₃H₇ | OCH₃ |
| Cl | (2-) OCH₃ | SCH₃ | OCH₃ |
| Cl | (2-) OCH₃ | SC₂H₅ | OCH₃ |
| Cl | (2-) OCH₃ | OCH₃ | OCH₃ |
| Cl | (2-) OCH₃ | OC₂H₅ | OCH₃ |
| Cl | (2-) OCH₃ | CH₃ | OC₂H₅ |
| Cl | (2-) OCH₃ | C₂H₅ | OC₂H₅ |
| Cl | (2-) OCH₃ | C₃H₇ | OC₂H₅ |
| Cl | (2-) OCH₃ | SCH₃ | OC₂H₅ |
| Cl | (2-) OCH₃ | SC₂H₅ | OC₂H₅ |
| Cl | (2-) OCH₃ | OCH₃ | OC₂H₅ |
| Cl | (2-) OCH₃ | OC₂H₅ | OC₂H₅ |
| SO₂CH₃ | (2-) OCH₃ | Cl | OCH₃ |
| SO₂CH₃ | (2-) OCH₃ | Br | OCH₃ |
| SO₂CH₃ | (2-) OCH₃ | CH₃ | OCH₃ |
| SO₂CH₃ | (2-) OCH₃ | C₂H₅ | OCH₃ |
| SO₂CH₃ | (2-) OCH₃ | C₃H₇ | OCH₃ |
| SO₂CH₃ | (2-) OCH₃ | SCH₃ | OCH₃ |
| SO₂CH₃ | (2-) OCH₃ | SC₂H₅ | OCH₃ |
| SO₂CH₃ | (2-) OCH₃ | OCH₃ | OC₂H₅ |
| SO₂CH₃ | (2-) OCH₃ | OC₂H₅ | OC₂H₅ |
| SO₂CH₃ | (2-) OCH₃ | CH₃ | OC₂H₅ |
| SO₂CH₃ | (2-) OCH₃ | C₂H₅ | OC₂H₅ |
| SO₂CH₃ | (2-) OCH₃ | C₃H₇ | OC₂H₅ |
| SO₂CH₃ | (2-) OCH₃ | SCH₃ | OC₂H₅ |
| SO₂CH₃ | (2-) OCH₃ | SC₂H₅ | OC₂H₅ |
| SO₂CH₃ | (2-) OCH₃ | OCH₃ | OC₂H₅ |
| Cl | (2-) F | OCH₃ | CH₃ |
| Cl | (2-) F | OCH₃ | C₂H₅ |
| Cl | (2-) F | C₂H₅ | OCH₃ |
| Cl | (2-) F | C₂H₅ | C₂H₅ |
| Cl | (2-) F | OC₂H₅ | CH₃ |
| Cl | (2-) F | OC₂H₅ | C₂H₅ |
| Cl | (2-) F | OCH₃ |  |
| Cl | (2-) F | OC₂H₅ |  |
| Cl | (2-) F | SCH₃ | CH₃ |
| Cl | (2-) F | SCH₃ |  |
| Cl | (2-) F | CH₃ | CH₃ |
| Cl | (2-) F | CH₃ |  |

Group 7

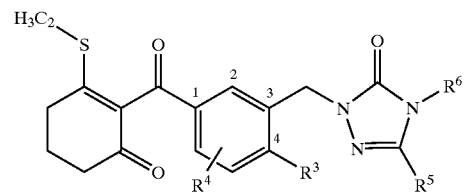

(IB-2)

Here, R³, R⁴, R⁵ and R⁶ each have, for example, the meanings given above in Group 6.

Group 8

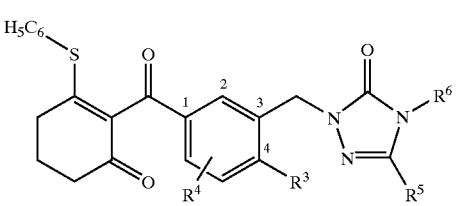

(IB-3)

Here, R³, R⁴, R⁵ and R⁶ each have, for example, the meanings given above in Group 6.

Group 9

(IB-4)

Here, R³, R⁴, R⁵ and R⁶ each have, for example, the meanings given above in Group 6.

Group 10

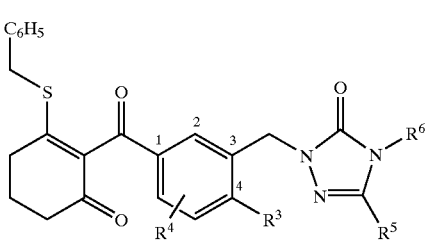

(IB-5)

Here, R³, R⁴, R₅ and R⁶ each have, for example, the meanings given above in Group 6.

The novel substituted benzoylcyclohexenones of the formula (I) have strong and selective herbicidal activity.

The novel substituted benzoylcyclohexenones of the formula (I) are obtained when substituted cyclohexanediones of the formula (II)

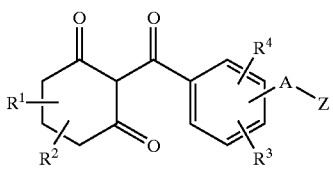

(II)

in which

A, $R^1$, $R^2$, $R^3$, $R^4$ and Z are as defined above, are reacted with a halogenating agent, if appropriate in the presence of a reaction auxiliary and if appropriate in the presence of a diluent, and the halogenocyclohexenones obtained in this way (in the first reaction step), of the formula (III)

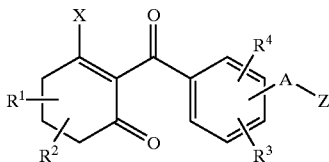

(III)

in which

A, $R^1$, $R^2$, $R^3$, $R^4$ and Z are as defined above,

X represents halogen, preferably represents fluorine or chlorine, particularly preferably represents chlorine, after intermediate isolation or without intermediate isolation ("in situ")

are reacted in a second reaction step with mercapto compounds of the formula (IV)

$$HS-Y \qquad (IV)$$

in which

Y is as defined above, if appropriate in the presence of a reaction auxiliary and if appropriate in the presence of a diluent, and, if appropriate, the compounds of the formula (I) obtained in this manner are subsequently subjected in a customary manner, within the scope of the definition of the substituents, to electrophilic or nucleophilic substitution reactions or oxidation or reduction reactions, or the compounds of the formula (I) are converted in a customary manner into salts.

Using, for example 2-[4-chloro-2-[(3,4-dimethyl-5-oxo-4,5-dihydro-1H-1,2,4-triazol-1-yl)-methyl]-benzoyl]-cyclohexane-1,3-dione and phosgene and then thiophenol as starting materials, the course of the reaction in the process according to the invention can be illustrated by the following equation

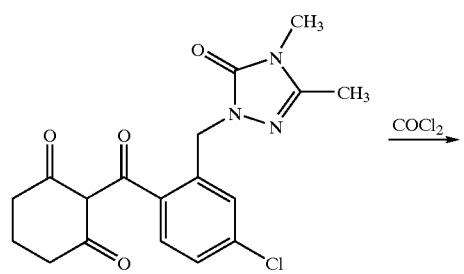

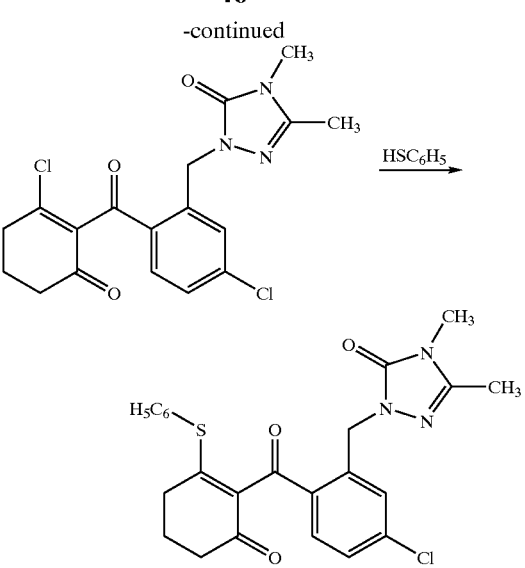

The formula (II) provides a general definition of the substituted benzoylcyclohexanediones to be used as starting materials in the process according to the invention for preparing compounds of the general formula (I). In the general formula (II), A, $R^1$, $R^2$, $R^3$, $R^4$ and Z each preferably have those meanings which have already been mentioned above, in connection with the description of the compounds of the general formula (I) according to the invention, as being preferred, particularly preferred, very particularly preferred or most preferred for A, $R^1$, $R^2$, $R^3$, $R^4$ and Z.

The starting materials of the general formula (II) are known and/or can be prepared by processes known per se (cf. WO-A-00/05221).

The first reaction step of the process according to the invention for preparing the compounds of the general of the general formula (I) is carried out using a halogenating agent. The halogenating agent used can be a customary halogenating agent suitable for converting enols into the corresponding halogenoalkenes. Here, halogen preferably represents fluorine, chlorine or bromine, in particular chlorine, i.e. preference is given to using chlorinating agents or brominating agents. These include, preferably, phosgene, oxalyl chloride, oxalyl bromide, phosphorus(III) chloride, phosphorus(III) bromide, phosphoryl chloride, thionyl chloride and thionyl bromide.

The first reaction step of the process according to the invention for preparing the compounds of the general formula (I) is preferably carried out using a reaction auxiliary. Suitable reaction auxiliaries are the reaction auxiliaries customarily used for halogenating reactions. These preferably include acetonitrile, N,N-dimethyl-formamide, N,N-diethyl-formamide, N,N-dipropyl-formamide and N,N-dibutyl-formamide, and also N-methyl-pyrrolidone.

The formula (IV) provides a general definition of the mercapto compounds further to be used as starting materials in the process according to the invention for preparing compounds of the general formula (I). In the general formula (IV), Y preferably has in particular that meaning which has already been mentioned above, in connection with the description of the compounds of the general formula (I) according to the invention, as being preferred, particularly preferred or very particularly preferred for Y.

The starting materials of the general formula (IV) are known organic chemicals for synthesis.

The second reaction step of the process according to the invention for preparing compounds of the general formula (I) is preferably carried out using a reaction auxiliary. Suitable reaction auxiliaries are, in general, the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide; furthermore also basic organic nitrogen compounds, such as, for example, trimethylamine, triethylamine, tripropylamine, tributylamine, ethyldiisopropylamine, N,N-dimethyl-cyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethylpyridine, 5-ethyl-2-methyl-pyridine, 4-dimethylamino-pyridine, N-methyl-piperidine, 1,4-diazabicyclo[2.2.2]-octane (DABCO), 1,5-diazabicyclo[4.3.0]-non-5-ene (DBN), or 1,8 diazabicyclo [5.4.0]-undec-7-ene (DBU).

The first and the second step of the process according to the invention for preparing the compounds of the general formula (I) are preferably carried out using diluents. Suitable diluents are especially inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or butyronitrile; amides, such as N,N-dimethylformamide, N,N-dimethylacetamide, N-methyl-formanilide, N-methyl-pyrrolidone or hexamethylphosphoric triamide; esters, such as methyl acetate or ethyl acetate; sulphoxides, such as dimethyl sulphoxide; alcohols, such as methanol, ethanol, n- or i-propanol, ethylene glycol monomethyl ether or ethylene glycol monoethyl ether.

When carrying out the first and the second step of the process according to the invention, the reaction temperatures can be varied within a relatively wide range. In general, the steps are carried out at temperatures between −20° C. and +150° C., preferably between 0° C. and 120° C.

The two steps of the process according to the invention are generally carried out under atmospheric pressure. However, it is also possible to carry out the process according to the invention under elevated or reduced pressure—in general between 0.1 bar and 10 bar.

For carrying out the process according to the invention, the starting materials are generally employed in approximately equimolar amounts. However, it is also possible to use a relatively large excess of one of the components. The reaction is generally carried out in a suitable diluent in the presence of a suitable reaction auxiliary and the reaction mixture is generally stirred at the required temperature for several hours. Work-up is carried out by customary methods (cf. the Preparation Examples).

The active compounds according to the invention can be used as defoliants, desiccants, haulm killers and, especially, as weed killers. Weeds in the broadest sense are understood to mean all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindemia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

Dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.*

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Monocotyledonous crops of the genera: *Allium, Ananas, Asparagus, Avena, Hordeum, Oryza, Panicum, Saecharum, Secale, Sorghum, Triticale, Triticum, Zea.*

However, the use of the active compounds according to the invention is in no way restricted to these genera, but also extends in the same manner to other plants.

The active compounds according to the invention are suitable, depending on the concentration, for the total control of weeds, for example on industrial terrain and rail tracks, and on paths and areas with and without tree plantings. Similarly, the active compounds according to the invention can be employed for controlling weeds in perennial crops, for example forests, decorative tree plantings, orchards, vineyards, citrus groves, nut orchards, banana plantations, coffee plantations, tea plantations, rubber plantations, oil palm plantations, cocoa plantations, soft fruit plantings and hop fields, on lawns, turf and pastureland, and for the selective control of weeds in annual crops.

The compounds of the formula (I) according to the invention have strong herbicidal activity and a broad activity spectrum when used on the soil or on above-ground parts of plants. To a certain extent, they are also suitable for the selective control of monocotyledonous and dicotyledonous weeds in monocotyledonous and dicotyledonous crops, both by the pre-emergence and by the post-emergence method.

At certain concentrations or application rates, the active compounds according to the invention can also be employed for controlling animal pests and fungal or bacterial plant diseases. If appropriate, they can also be used as intermediates or precursors for the synthesis of other active compounds.

According to the invention, it is possible to treat all plants and parts of plants. Plants are to be understood here as meaning all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant breeders' certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested plants and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multi-layer coating.

The active compounds can be converted into the customary formulations, such as solutions, emulsions, wettable powders, suspensions, powders, dusts, pastes, soluble powders, granules, suspo-emulsion concentrates, natural and synthetic substances impregnated with active compound, and microencapsulations in polymeric substances.

These formulations are produced in a known manner, for example by mixing the active compounds with extenders, that is to say liquid solvents and/or solid carriers, optionally with the use of surfactants, that is to say emulsifiers and/or dispersants and/or foam formers.

If the extender used is water, it is also possible to use, for example, organic solvents as auxiliary solvents. Liquid solvents which are mainly suitable are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks, such as calcite, marble, pumice, sepiolite, dolomite and synthetic granules of inorganic and organic meals, and granules of organic material, such as sawdust, coconut shells, maize cobs and tobacco stalks; suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Tackifiers, such as carboxymethylcellulose, natural and synthetic polymers in the form of powders, granules or latices, such as gum arabic, polyvinyl alcohol and polyvinyl acetate, and also natural phospholipids, such as cephalins and lecithins, and synthetic phospholipids can be used in the formulations. Other possible additives are mineral and vegetable oils.

It is possible to use colorants, such as inorganic pigments, for example iron oxide, titanium oxide, Prussian blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations generally comprise between 0.1 and 95 percent by weight of active compound, preferably between 0.5 and 90%.

For controlling weeds, the active compounds according to the invention, as such or in their formulations, can also be used as mixtures with known herbicides and/or substances which improve the compatibility with crop plants ("safeners"), finished formulations or tank mixes being possible. Also possible are mixtures with weed-killers comprising one or more known herbicides and a safener.

Possible components for the mixtures are known herbicides, for example acetochlor, acifluorfen (-sodium), aclonifen, alachlor, alloxydim (-sodium), ametryne, amicarbazone, amidochlor, amidosulfuron, anilofos, asulam, atrazine, azafenidin, azimsulfuron, beflubutamid, benazolin (-ethyl), benfuresate, bensulfuron (-methyl), bentazon, benzfendizone, benzobicyclon, benzofenap, benzoylprop(-ethyl), bialaphos, bifenox, bispyribac (-sodium), bromobutide, bromofenoxim, bromoxynil, butachlor, butafenacil (-allyl), butroxydim, butylate, cafenstrole, caloxydim, carbetamide, carfentrazone (-ethyl), chlomethoxyfen, chloramben, chloridazon, chlorimuron (-ethyl), chlomitrofen, chlorsulfuron, chlortoluron, cinidon (-ethyl), cinmethylin, cinosulfuron, clefoxydim, clethodim, clodinafop (-propargyl), clomazone, clomeprop, clopyralid, clopyrasulfuron (-methyl), cloransulam (-methyl), cumyluron, cyanazine, cybutryne, cycloate, cyclosulfamuron, cycloxydim, cyhalofop (-butyl), 2,4-D, 2,4-DB, desmedipham, diallate, dicamba, dichlorprop (-P), diclofop (-methyl), diclosulam, diethatyl (-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulfuron (-methyl), ethofumesate, ethoxyfen, ethoxysulfuron, etobenzanid, fenoxaprop (-P-ethyl), fentrazamide, flamprop (-isopropyl, -isopropyl-L, -methyl), flazasulfuron, florasulam, fluazifop (-P-butyl), fluazolate, flucarbazone (-sodium), flufenacet, flumetsulam, flumiclorac (-pentyl), flumioxazin, flumipropyn, flumetsulam, fluometuron, fluorochloridone, fluoroglycofen (-ethyl), flupoxam, flupropacil, flurpyrsulfuron (-methyl, -sodium), flurenol (-butyl), fluridone, fluroxypyr (-butoxypropyl, -meptyl), flurprimidol, flurtamone, fluthiacet (-methyl), fluthiamide, fomesafen, foramsulfuron, glufosinate (-ammonium), glyphosate (-isopropylammonium), halosafen, haloxyfop (-ethoxyethyl, -P-methyl), hexazinone, imazamethabenz (-methyl), imazamethapyr, imazamox, imazapic, imazapyr, imazaquin, imazethapyr, imazosulfuron, iodosulfuron (-methyl, -sodium), ioxynil, isopropalin, isoproturon, isouron, isoxaben, isoxachlortole, isoxaflutole, isoxapyrifop, lactofen, lenacil, linuron, MCPA, mecoprop, mefenacet, mesotrione, metamitron, metazachlor, methabenzthiazuron, metobenzuron, metobromuron, (alpha-)metolachlor, metosulam, metoxuron, metribuzin, metsulfuron (-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, pentoxazone, phemnedipham, picolinafen, piperophos, pretilachlor, primisulfuron (-methyl), profluazol, prometryn, propachlor, propanil, propaquizafop, propisochlor, procarbazone (-sodium), propyzamide, prosulfocarb, prosulfuron, pyraflufen (-ethyl), pyrazogyl, pyrazolate, pyrazosulfuron (-ethyl), pyrazoxyfen, pyribenzoxim, pyributicarb, pyridate, pyridatol, pyriftalid, pyriminobac (-methyl), pyrithiobac (-sodium), quinchlorac, quinmerac, quinoclamine, quizalofop (-P-ethyl, -P-tefuryl), rimsulfuron, sethoxydim, simazine, simetryn, sulcotrione, sulfentrazone, sulfometuron (-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron (-methyl), thiobencarb, tiocarbazil, tralkoxydim, triallate, triasulfuron, tribenuron (-methyl), triclopyr, tridiphane, trifluralin, trifloxysulfuron, triflusulfuron (-methyl), tritosulfuron.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms, prepared therefrom by further dilution, such as ready-to-use solutions, suspensions, emulsions, powders, pastes and granules. They are used in a customary manner, for example by watering, spraying, atomizing or broadcasting.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The preparation and the use of the active compounds according to the invention is illustrated by the examples below.

PREPARATION EXAMPLES

Example 1

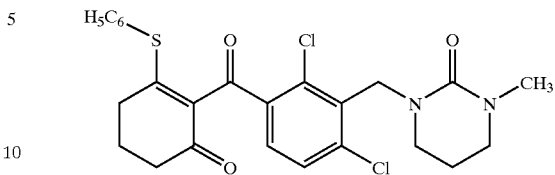

A mixture of 1.3 g (3 mmol) of 2-[2,4-dichloro-3-[(3-methyl-2-oxo-tetrahydro-1(2H)-pyrimidinyl)-methyl]-benzoyl]-cyclohexane-1,3-dione, 1.0 g (7.5 mmol) of oxalyl chloride, 2 drops of N,N-dimethyl-formamide and 30 ml of methylene chloride is heated under reflux for 30 minutes and then concentrated under water pump vacuum. The residue is taken up in 50 ml of tetrahydrofuran and admixed with 0.33 g (3 mmol) of thiophenol. With ice-cooling, 0.50 g (4.5 mmol) of triethylamine is then added dropwise. The ice-cooling is removed, and the mixture is then stirred at room temperature for 2 hours and subsequently concentrated under water pump vacuum. The residue is taken up in methylene chloride, washed once each with 1N hydrochloric acid, water and saturated aqueous sodium chloride solution, dried with sodium sulphate and filtered. The filtrate is concentrated under water pump vacuum, the residue is digested with diethyl ether and the resulting crystalline product is isolated by filtration with suction.

This gives 0.91 g (61% of theory) of 1-[2,6-dichloro-3-[(6-oxo-2-phenylthio-1-cyclohexen-1-yl)-carbonyl]-benzyl]-3-methyl-tetrahydro-2(1H)-pyrimidinone of melting point 140° C.

Analogously to Example 1 and in accordance with the general description of the preparation process according to the invention, it is also possible to prepare, for example, the compounds of the general formula (I)—or those of the general formula (ID)—listed in Table 1 below.

TABLE 1

Examples of compounds of the formula (ID)

(ID)

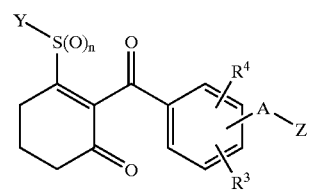

| Ex. No. | n | (position) $R^3$ | (position) $R^4$ | (position) —A-Z | Y | Physical data |
|---|---|---|---|---|---|---|
| 2 | 0 | (2) Cl | (4) Cl | (3) 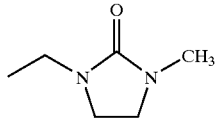 | $C_6H_5$ | m.p.: 169° C. logP = 3.02[a] |

TABLE 1-continued

Examples of compounds of the formula (ID)

(ID)

| Ex. No. | n | (position) R³ | (position) R⁴ | (position) —A-Z | Y | Physical data |
|---|---|---|---|---|---|---|
| 3 | 0 | (2) Cl | (4) Cl | (3) 1,3-diethyl-imidazolidin-2-one | C₆H₅ | m.p.: 149° C. logP = 3.30[a] |
| 4 | 0 | (2) Cl | (4) Cl | (3) 2-ethyl-4-methyl-5-(methylthio)-2,4-dihydro-3H-1,2,4-triazol-3-one | C₆H₅ | m.p.: 159° C. logP = 3.29[a] |
| 5 | 0 | (2) Cl | (4) Cl | (3) 4,5-dicyclopropyl-2-ethyl-2,4-dihydro-3H-1,2,4-triazol-3-one | C₆H₅ | m.p.: 163° C. logP = 3.50[a] |
| 6 | 0 | (2) Cl | (4) SO₂CH₃ | (3) 2-ethyl-4-methyl-5-(methylthio)-2,4-dihydro-3H-1,2,4-triazol-3-one | C₆H₅ | m.p.: 195° C. logP = 2.84[a] |
| 7 | 0 | (2) Cl | (4) SO₂CH₃ | (3) 2-ethyl-5-methoxy-4-methyl-2,4-dihydro-3H-1,2,4-triazol-3-one | C₆H₅ | m.p.: 234° C. logP = 2.67[a] |

TABLE 1-continued

Examples of compounds of the formula (ID)

(ID)

| Ex. No. | n | (position) R³ | (position) R⁴ | (position) —A-Z | Y | Physical data |
|---|---|---|---|---|---|---|
| 8 | 0 | (2) Cl | (4) SO₂CH₃ | (3) [1-ethyl-3-methyl-imidazolidin-2-one] | C₆H₅ | m.p.: 203° C. logP = 2.56[a] |
| 9 | 0 | (2) Cl | (4) SO₂CH₃ | (3) [1,3-diethyl-imidazolidin-2-one] | C₆H₅ | m.p.: 184° C. logP = 2.79[a] |
| 10 | 0 | (2) Cl | (4) SO₂CH₃ | (3) [1-ethyl-4-ethoxy-5-ethyl-1,2,4-triazol-3-one] | C₆H₅ | m.p.: 228° C. logP = 3.13[a] |
| 11 | 0 | (2) Cl | (4) Cl | (3) [1-ethyl-4-methyl-5-methoxy-1,2,4-triazol-3-one] | C₆H₅ | m.p.: 176° C. logP = 3.06[a] |

TABLE 1-continued

Examples of compounds of the formula (ID)

(ID)

| Ex. No. | n | (position) R³ | (position) R⁴ | (position) —A-Z | Y | Physical data |
|---|---|---|---|---|---|---|
| 12 | 0 | (2) Cl | (4) Cl | (3) [1-ethyl-4-methyl-5-isopropoxy-1,2,4-triazol-3(4H)-one] | C₆H₅ | m.p.: 145° C. logP = 3.69[a] |
| 13 | 0 | (2) Cl | (4) Cl | (3) [1-ethyl-4-methyl-5-dimethylamino-1,2,4-triazol-3(4H)-one] | C₆H₅ | m.p.: 207° C. logP = 3.10[a] |
| 14 | 2 | (2) Cl | (4) Cl | (3) [1-ethyl-4-methyl-5-methoxy-1,2,4-triazol-3(4H)-one] | C₆H₅ | m.p.: 180° C. logP = 2.62[a] |
| 15 | 1 | (2) Cl | (4) Cl | (3) [1-ethyl-4-methyl-5-methoxy-1,2,4-triazol-3(4H)-one] | C₆H₅ | |

TABLE 1-continued

Examples of compounds of the formula (ID)

(ID)

| Ex. No. | n | (position) R³ | (position) R⁴ | (position) —A-Z | Y | Physical data |
|---|---|---|---|---|---|---|
| 16 | 0 | (4) CF₃ | — | (2) 1-ethyl-4-methyl-5-(SCH₃)-1,2,4-triazol-3(4H)-one | $C_6H_5$ | logP = 3.58[a] |
| 17 | 0 | (4) CF₃ | — | (2) 1-ethyl-4-methyl-5-(SCH₃)-1,2,4-triazol-3(4H)-one | $CH_3$ | logP = 2.63[a] |
| 18 | 0 | (4) CF₃ | — | (2) 1-ethyl-4-methyl-5-(OCH₃)-1,2,4-triazol-3(4H)-one | $C_6H_5$ | logP = 3.30[a] |
| 19 | 0 | (4) CF₃ | — | (2) 1-ethyl-4-methyl-5-(OCH₃)-1,2,4-triazol-3(4H)-one | $CH_3$ | logP = 2.41[a] |
| 20 | 0 | (4) CF₃ | — | (2) 1-ethyl-2-methyl-4-methyl-1,2,4-triazolidine-3,5-dione | $C_6H_5$ | logP = 3.25[a] |
| 21 | 0 | (2) Cl | (4) Cl | (3) 1-ethyl-4-methyl-tetrazol-5(4H)-one | $C_6H_5$ | |

TABLE 1-continued

Examples of compounds of the formula (ID)

(ID)

| Ex. No. | n | (position) R³ | (position) R⁴ | (position) —A-Z | Y | Physical data |
|---|---|---|---|---|---|---|
| 22 | 0 | (2) Cl | (4) SO₂CH₃ | (3) 1-ethyl-4-(1-methylcyclopropyl)-tetrazol-5-one | C₆H₅ | |
| 23 | 0 | (2) Cl | (4) SO₂CH₃ | (3) 1-ethyl-4-cyclopropyl-tetrazol-5-one | C₆H₅ | |
| 24 | 0 | (2) Cl | (4) Cl | (3) 1-ethyl-4-ethyl-tetrazol-5-one | C₆H₅ | |
| 25 | 0 | (2) Cl | (4) Cl | (3) 1-ethyl-4-cyclopropyl-tetrazol-5-one | C₆H₅ | |
| 26 | 0 | (2) Cl | (4) SO₂CH₃ | (3) 1-ethyl-4-ethyl-tetrazol-5-one | C₆H₅ | |
| 27 | 0 | (2) Cl | (4) Cl | (3) 1-ethyl-3-n-propyl-imidazolidin-2-one | C₆H₅ | |
| 28 | 0 | (2) Cl | (4) Cl | (3) 1-ethyl-3-i-propyl-imidazolidin-2-one | C₆H₅ | |

TABLE 1-continued
Examples of compounds of the formula (ID)
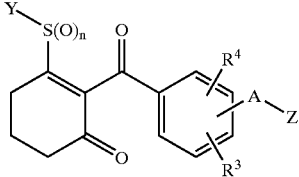
(ID)
| Ex. No. | n | (position) R³ | (position) R⁴ | (position) —A-Z | Y | Physical data |
|---|---|---|---|---|---|---|
| 29 | 0 | (2) Cl | (4) Cl | (3) 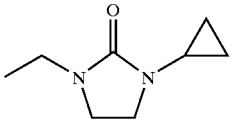 | $C_6H_5$ | |
| 30 | 0 | (2) Cl | (4) Cl | (3) 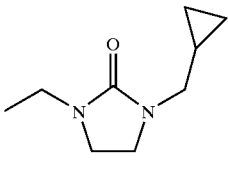 | $C_6H_5$ | |
| 31 | 0 | (2) Cl | (4) Cl | (3) 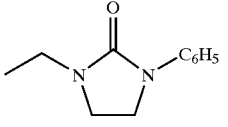 | $C_6H_5$ | |
| 32 | 0 | (2) Cl | (4) Cl | (3) 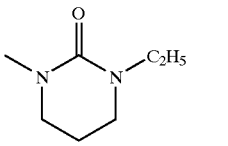 | $C_6H_5$ | |
| 33 | 0 | (2) Cl | (4) Cl | (3) 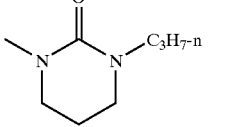 | $C_6H_5$ | |
| 34 | 0 | (2) Cl | (4) Cl | (3)  | $C_6H_5$ | |

TABLE 1-continued

Examples of compounds of the formula (ID)

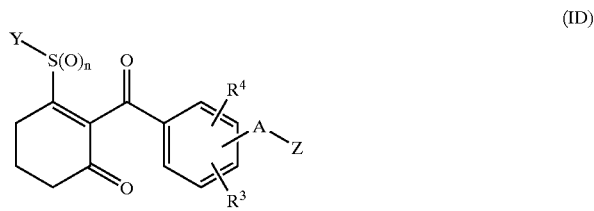

(ID)

| Ex. No. | n | (position) R³ | (position) R⁴ | (position) —A-Z | | Y | Physical data |
|---|---|---|---|---|---|---|---|
| 35 | 0 | (2) Cl | (4) Cl | (3) | N-methyl-N'-isopropyl cyclic urea | $C_6H_5$ | |
| 36 | 0 | (2) Cl | (4) Cl | (3) | N-methyl-N'-cyclopropyl cyclic urea | $C_6H_5$ | |
| 37 | 0 | (2) Cl | (4) Cl | (3) | N-methyl-N'-tert-butyl cyclic urea | $C_6H_5$ | |
| 38 | 0 | (2) Cl | (4) Cl | (3) | N-methyl-N'-cyclopropylmethyl cyclic urea | $C_6H_5$ | |
| 39 | 0 | (2) Cl | (4) $SO_2CH_3$ | (3) | N-ethyl-N'-cyclopropyl imidazolidinone | $C_6H_5$ | |
| 40 | 0 | (2) Cl | (4) $SO_2CH_3$ | (3) | N,N'-dimethyl cyclic urea | $C_6H_5$ | |
| 41 | 0 | (2) Cl | (4) $SO_2CH_3$ | (3) | N-methyl-N'-ethyl cyclic urea | $C_6H_5$ | |

TABLE 1-continued
Examples of compounds of the formula (ID)
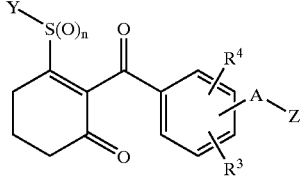
(ID)
| Ex. No. | n | (position) R³ | (position) R⁴ | (position) —A-Z | Y | Physical data |
|---|---|---|---|---|---|---|
| 42 | 0 | (2) OCH₃ | (4) Cl | (3) 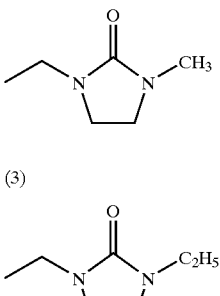 | C₆H₅ | |
| 43 | 0 | (2) OCH₃ | (4) Cl | (3) 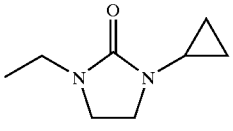 | C₆H₅ | |
| 44 | 0 | (2) OCH₃ | (4) Cl | (3) 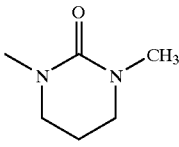 | C₆H₅ | |
| 45 | 0 | (2) OCH₃ | (4) Cl | (3) 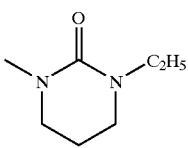 | C₆H₅ | |
| 46 | 0 | (2) OCH₃ | (4) Cl | (3) | C₆H₅ | |

TABLE 1-continued
Examples of compounds of the formula (ID)
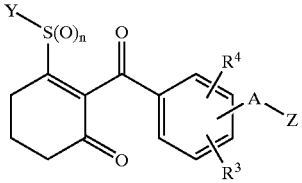
| Ex. No. | n | (position) R³ | (position) R⁴ | (position) —A-Z | | Y | Physical data |
|---|---|---|---|---|---|---|---|
| 47 | 0 | (2) Cl | (4) CF₃ | (3) | 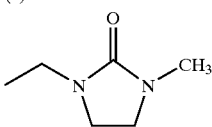 | C₆H₅ | |
| 48 | 0 | (2) Cl | (4) CF₃ | (3) | 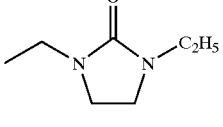 | C₆H₅ | |
| 49 | 0 | (2) Cl | (4) CF₃ | (3) | 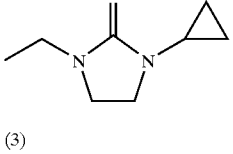 | C₆H₅ | |
| 50 | 0 | (2) Cl | (4) CF₃ | (3) | 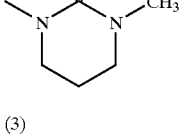 | C₆H₅ | |
| 51 | 0 | (2) Cl | (4) CF₃ | (3) | 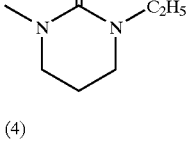 | C₆H₅ | |
| 52 | 0 | (2) Cl | — | (4) | 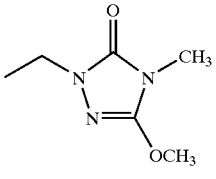 | C₆H₅ | |
| 53 | 0 | (2) OCH₃ | (4) Cl | (3) | 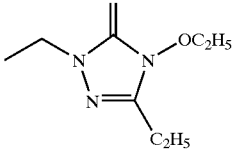 | C₆H₅ | |

TABLE 1-continued

Examples of compounds of the formula (ID)

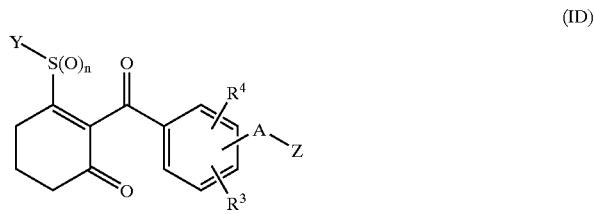

| Ex. No. | n | (position) R³ | (position) R⁴ | (position) —A-Z | Y | Physical data |
|---|---|---|---|---|---|---|
| 54 | 0 | (2) OCH₃ | (4) Cl | (3) ethyl-imidazolidinone-C₃H₇-i | C₆H₅ | |
| 55 | 0 | (2) OCH₃ | (4) Cl | (3) methyl-tetrahydropyrimidinone-C₃H₇-i | C₆H₅ | |
| 56 | 0 | (2) Cl | (4) SO₂CH₃ | (3) ethyl-tetrazolinone-CH₃ | C₆H₅ | m.p.: 85° C. |
| 57 | 0 | (2) Cl | (4) SO₂CH₃ | (3) ethyl-tetrazolinone-CH₃ | C₆H₅ | m.p.: 226° C. |
| 58 | 0 | (2) Cl | — | (4) ethyl-tetrazolinone-CH₃ | C₆H₅ | m.p.: 183° C. |
| 59 | 0 | (2) Cl | (4) SO₂CH₃ | (3) ethyl-tetrazolinone-C(CH₃)₃ | C₆H₅ | m.p.: 159° C. |
| 60 | 0 | (2) NO₂ | — | (4) ethyl-tetrazolinone-CH₃ | C₆H₅ | m.p.: 77° C. |

TABLE 1-continued

Examples of compounds of the formula (ID)

(ID)

| Ex. No. | n | (position) R³ | (position) R⁴ | (position) —A-Z | Y | Physical data |
|---|---|---|---|---|---|---|
| 61 | 0 | (4) CF₃ | — | (2) ethyl-methyl-tetrazolinone | C₆H₅ | m.p.: 167° C. |
| 62 | 0 | (2) Cl | (4) Cl | (3) ethyl-cyclopropyl-tetrazolinone | C₂H₅ | $n_D^{20} = 1.6122$ |
| 63 | 0 | (2) Cl | (4) Cl | (3) ethyl-cyclopropyl-tetrazolinone | CH₃ | $n_D^{20} = 1.6018$ |
| 64 | 0 | (2) Cl | (4) SO₂CH₃ | (3) ethyl-isopropyl-imidazolidinone | C₆H₅ | m.p.: 116° C. |
| 65 | 0 | (2) Cl | — | (4) ethyl-methyl-tetrazolinone | C₆H₅ | m.p.: 88° C. |
| 66 | 0 | (2) Cl | — | (4) ethyl-cyclopropyl-tetrazolinone | C₆H₅ | m.p.: 59° C. |
| 67 | 0 | (2) Cl | (4) SCH₃ | (3) ethyl-methyl-tetrazolinone | CH₃ | m.p.: 82° C. |

TABLE 1-continued

Examples of compounds of the formula (ID)

(ID)

| Ex. No. | n | (position) R³ | (position) R⁴ | (position) —A-Z | Y | Physical data |
|---|---|---|---|---|---|---|
| 68 | 0 | (2) Cl | (4) SC₂H₅ | (3) [1-ethyl-4-methyl-tetrazol-5-one] | C₂H₅ | m.p.: 64° C. |
| 69 | 0 | (2) Cl | (4) SO₂CH₃ | (3) [1-ethyl-4-methyl-tetrazol-5-one] | CH₃ | m.p.: 100° C. |
| 70 | 0 | (2) Cl | (4) SO₂CH₃ | (3) [1-ethyl-4-methyl-tetrazol-5-one] | (CH₃)₂C=CH-CH₂- (2-methyl-2-butenyl) | m.p.: 96° C. |
| 71 | 0 | (4) F | — | (2) [1-ethyl-4-methyl-tetrazol-5-one] | C₆H₅ | |
| 72 | 0 | (4) Cl | — | (2) [1-ethyl-4-methyl-tetrazol-5-one] | C₆H₅ | |
| 73 | 0 | (4) Br | — | (2) [1-ethyl-4-methyl-tetrazol-5-one] | C₆H₅ | |
| 74 | 0 | (4) I | — | (2) [1-ethyl-4-methyl-tetrazol-5-one] | C₆H₅ | |

TABLE 1-continued

Examples of compounds of the formula (ID)

(ID)

| Ex. No. | n | (position) R³ | (position) R⁴ | (position) —A-Z | Y | Physical data |
|---------|---|---------------|---------------|-----------------|---|---------------|
| 75 | 0 | (4) CN | — | (2) [1-ethyl-4-methyl-tetrazol-5(4H)-one] | $C_6H_5$ | |
| 76 | 0 | (4) $CF_3$ | — | (2) [1-ethyl-4-ethyl-tetrazol-5(4H)-one] | $C_6H_5$ | |
| 77 | 0 | (4) $CF_3$ | — | (2) [1-ethyl-4-cyclopropyl-tetrazol-5(4H)-one] | $C_6H_5$ | |
| 78 | 0 | (2) Cl | (4) Cl | (3) [1-ethyl-4-n-propyl-tetrazol-5(4H)-one] | $C_6H_5$ | |
| 79 | 0 | (2) Cl | (4) Cl | (3) [1-ethyl-4-i-propyl-tetrazol-5(4H)-one] | $C_6H_5$ | |
| 80 | 0 | (2) Cl | (4) Cl | (3) [1-ethyl-4-vinyl-tetrazol-5(4H)-one] | $C_6H_5$ | |
| 81 | 0 | (2) Cl | (4) Cl | (3) [1-ethyl-4-methyl-tetrazol-5(4H)-one] | $CH_3$ | |

TABLE 1-continued

Examples of compounds of the formula (ID)

(ID)

| Ex. No. | n | (position) R³ | (position) R⁴ | (position) —A-Z | Y | Physical data |
|---|---|---|---|---|---|---|
| 82 | 0 | (2) Cl | (4) Cl | (3) [1,4-diethyl-tetrazol-5(4H)-one] | CH₃ | |
| 83 | 0 | (2) Cl | (4) Cl | (3) [1-ethyl-4-vinyl-tetrazol-5(4H)-one] | CH₃ | |
| 84 | 0 | (2) Cl | (4) Cl | (3) [1-ethyl-4-methyl-tetrazol-5(4H)-one] | C₂H₅ | |
| 85 | 0 | (2) Cl | (4) Cl | (3) [1,4-diethyl-tetrazol-5(4H)-one] | C₂H₅ | |
| 86 | 0 | (2) Cl | (4) Cl | (3) [1-ethyl-4-vinyl-tetrazol-5(4H)-one] | C₂H₅ | |
| 87 | 0 | (2) Cl | (4) SO₂CH₃ | (3) [1-ethyl-4-n-propyl-tetrazol-5(4H)-one] | C₆H₅ | |
| 88 | 0 | (2) Cl | (4) SO₂CH₃ | (3) [1-ethyl-4-vinyl-tetrazol-5(4H)-one] | C₆H₅ | |

TABLE 1-continued

Examples of compounds of the formula (ID)

| Ex. No. | n | (position) R³ | (position) R⁴ | (position) —A-Z | Y | Physical data |
|---|---|---|---|---|---|---|
| 89 | 0 | (2) Cl | (4) SO₂CH₃ | (3) 1,4-disubstituted tetrazol-5(4H)-one with N-ethyl and N-CH₂CF₃ | C₆H₅ | |
| 90 | 0 | (2) Cl | (4) SO₂CH₃ | (3) 1,4-disubstituted tetrazol-5(4H)-one with N-ethyl and N-C₂H₅ | CH₃ | |
| 91 | 0 | (2) Cl | (4) SO₂CH₃ | (3) 1,4-disubstituted tetrazol-5(4H)-one with N-ethyl and N-cyclopropyl | CH₃ | |
| 92 | 0 | (2) Cl | (4) SO₂CH₃ | (3) 1,4-disubstituted tetrazol-5(4H)-one with N-ethyl and N-vinyl | CH₃ | |
| 93 | 0 | (2) Cl | (4) SO₂CH₃ | (3) 1,4-disubstituted tetrazol-5(4H)-one with N-ethyl and N-C₂H₅ | C₂H₅ | |
| 94 | 0 | (2) Cl | (4) SO₂CH₃ | (3) 1,4-disubstituted tetrazol-5(4H)-one with N-ethyl and N-cyclopropyl | C₂H₅ | |
| 95 | 0 | (2) Cl | (4) SO₂CH₃ | (3) 1,4-disubstituted tetrazol-5(4H)-one with N-ethyl and N-vinyl | C₂H₅ | |

TABLE 1-continued

Examples of compounds of the formula (ID)

(ID)

| Ex. No. | n | (position) R³ | (position) R⁴ | (position) —A-Z | Y | Physical data |
|---|---|---|---|---|---|---|
| 96 | 0 | (2) Br | (4) Br | (3) 1-ethyl-4-methyl-tetrazol-5(4H)-one | $C_6H_5$ | m.p.: 94° C. |
| 97 | 0 | (2) Br | (4) Br | (3) 1-ethyl-4-ethyl-tetrazol-5(4H)-one | $C_6H_5$ | |
| 98 | 0 | (2) Br | (4) Br | (3) 1-ethyl-4-cyclopropyl-tetrazol-5(4H)-one | $C_6H_5$ | m.p.: 86° C. |
| 99 | 0 | (2) Br | (4) Br | (3) 1-ethyl-4-methyl-tetrazol-5(4H)-one | $CH_3$ | |
| 100 | 0 | (2) Br | (4) Br | (3) 1-ethyl-4-methyl-tetrazol-5(4H)-one | $C_2H_5$ | |
| 101 | 0 | (2) $CH_3$ | (4) $SO_2CH_3$ | (3) 1-ethyl-4-methyl-tetrazol-5(4H)-one | $C_6H_5$ | |
| 102 | 0 | (2) $CH_3$ | (4) $SO_2CH_3$ | (3) 1-ethyl-4-ethyl-tetrazol-5(4H)-one | $C_6H_5$ | |

TABLE 1-continued

Examples of compounds of the formula (ID)

(ID)

| Ex. No. | n | (position) R³ | (position) R⁴ | (position) —A-Z | Y | Physical data |
|---------|---|---------------|---------------|-----------------|---|---------------|
| 103 | 0 | (2) CH₃ | (4) SO₂CH₃ | (3) 1-ethyl-4-cyclopropyl-tetrazol-5-one | C₆H₅ | |
| 104 | 0 | (2) CH₃ | (4) SO₂CH₃ | (3) 1-ethyl-4-methyl-tetrazol-5-one | CH₃ | |
| 105 | 0 | (2) CH₃ | (4) SO₂CH₃ | (3) 1-ethyl-4-methyl-tetrazol-5-one | C₂H₅ | |
| 106 | 0 | (2) CH₃ | (4) SO₂CH₃ | (3) 1-ethyl-4-methyl-tetrazol-5-one | C₆H₅ | |
| 107 | 0 | (2) OCH₃ | (4) Cl | (3) 1-ethyl-4-ethyl-tetrazol-5-one | C₆H₅ | |
| 108 | 0 | (2) OCH₃ | (4) Cl | (3) 1-ethyl-4-cyclopropyl-tetrazol-5-one | C₆H₅ | |
| 109 | 0 | (2) OCH₃ | (4) Cl | (3) 1-ethyl-4-methyl-tetrazol-5-one | CH₃ | |

TABLE 1-continued
Examples of compounds of the formula (ID)
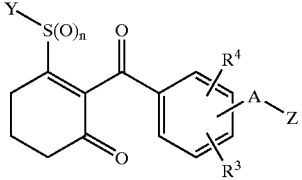
| Ex. No. | n | (position) R³ | (position) R⁴ | (position) —A-Z | Y | Physical data |
|---|---|---|---|---|---|---|
| 110 | 0 | (2) OCH₃ | (4) Cl | (3) 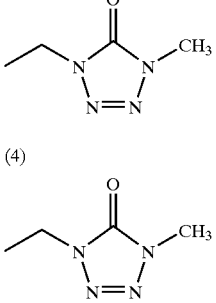 | C₂H₅ | |
| 111 | 0 | (2) Br | — | (4) 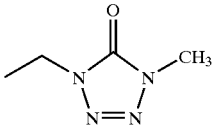 | C₆H₅ | |
| 112 | 0 | (2) I | — | (4) 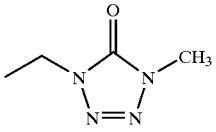 | C₆H₅ | |
| 113 | 0 | (2) CF₃ | — | (4) 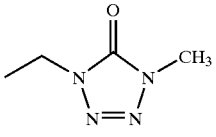 | C₆H₅ | |
| 114 | 0 | (2) CN | — | (4) 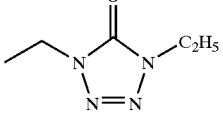 | C₆H₅ | |
| 115 | 0 | (2) NO₂ | — | (4) 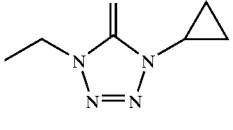 | C₆H₅ | |
| 116 | 0 | (2) NO₂ | — | (4)  | C₆H₅ | |

TABLE 1-continued

Examples of compounds of the formula (ID)

(ID)

| Ex. No. | n | (position) R³ | (position) R⁴ | (position) —A-Z | Y | Physical data |
|---|---|---|---|---|---|---|
| 117 | 0 | (2) NO₂ | — | (4) [ethyl-vinyl-tetrazolinone] | C₆H₅ | |
| 118 | 0 | (2) NO₂ | — | (4) [ethyl-methyl-tetrazolinone] | CH₃ | |
| 119 | 0 | (2) NO₂ | — | (4) [ethyl-methyl-tetrazolinone] | C₂H₅ | |
| 120 | 0 | (2) Cl | (4) Cl | (3) [ethyl-n-butyl-imidazolidinone] | C₆H₅ | m.p.: 154° C. logP = 4.02[a] |
| 121 | 0 | (2) Cl | (4) Cl | (3) [ethyl-i-butyl-imidazolidinone] | C₆H₅ | m.p.: 156° C. logP = 3.98[a] |
| 122 | 0 | (2) Cl | (4) SO₂CH₃ | (3) [methyl-i-propyl-tetrahydropyrimidinone] | C₆H₅ | logP = 3.11[a] |

The logP values given in Table 1 were determined in accordance with EEC Directive 79/831 Annex V.A8 by HPLC (High Performance Liquid Chromatography) using a reversed-phase column (C 18). Temperature: 43° C.

(a) Mobile phases for the determination in the acidic range: 0.1% aqueous phosphoric acid, acetonitrile; linear gradient from 10% acetonitrile to 90% acetonitrile—the corresponding data are labelled [a] in Table 1.

(b) Mobile phases for the determination in the neutral range: 0.01 molar aqueous phosphate buffer solution, acetonitrile; linear gradient from 10% acetonitrile to 90% acetonitrile—corresponding data are labelled [b] in Table 1.

Calibration was carried out using unbranched alkan-2-ones (having 3 to 16 carbon atoms), with known logP values (determination of the logP values by the retention times using linear interpolation between two successive alkanones).

The lambda max values were determined in the maxima of the chromatographic signals, using the UV spectra from 200 nm to 400 nm.

TABLE 2

Further examples of the compounds of the formula (I)

(I)

| Ex No. | n | (position) R1, R2 | (position) R3 | (position) R4 | (position) —A-Z | Y | Physical data |
|---|---|---|---|---|---|---|---|
| 123 | 0 | (4) CH$_3$,<br>(4) CH$_3$ | (2) Cl | (4) Cl | (3) 1-ethyl-4-methyl-tetrazol-5(4H)-one | C$_6$H$_5$ | m.p.: 77° C. |
| 124 | 0 | (5) CH$_3$,<br>(5) CH$_3$ | (2) Cl | (4) Cl | (3) 1-ethyl-4-methyl-tetrazol-5(4H)-one | C$_6$H$_5$ | m.p.: 85° C. |
| 125 | 0 | (4) CH$_3$,<br>(4) CH$_3$ | (2) Cl | (4) SO$_2$CH$_3$ | (3) 1-ethyl-4-methyl-tetrazol-5(4H)-one | C$_6$H$_5$ | m.p.: 99° C. |
| 126 | 0 | (5) CH$_3$,<br>(5) CH$_3$ | (2) Cl | (4) SO$_2$CH$_3$ | (3) 1-ethyl-4-methyl-tetrazol-5(4H)-one | C$_6$H$_5$ | m.p.: 104° C. |
| 127 | 0 | (3)<br>—CH$_2$CH$_2$—<br>(5) | (2) Cl | (4) Cl | (3) 1-ethyl-4-cyclopropyl-tetrazol-5(4H)-one | C$_6$H$_5$ | m.p.: 84° C. |
| 128 | 0 | (3)<br>—CH$_2$CH$_2$—<br>(5) | (4) Br | — | (2) 1-ethyl-4-methyl-tetrazol-5(4H)-one | C$_6$H$_5$ | m.p.: 186° C. |
| 129 | 0 | (3)<br>—CH$_2$CH$_2$—<br>(5) | (4) CF$_3$ | — | (2) 1-ethyl-4-methyl-tetrazol-5(4H)-one | C$_6$H$_5$ | m.p.: 197° C. |

TABLE 2-continued

Further examples of the compounds of the formula (I)

| Ex No. | n | (position) R$^1$, R2 | (position) R$^3$ | (position) R$^4$ | (position) —A-Z | Y | Physical data |
|---|---|---|---|---|---|---|---|
| 130 | 0 | (3) —CH$_2$CH$_2$— (5) | (2) NO$_2$ | — | (4) 1-ethyl-4-methyl-tetrazol-5(4H)-one | C$_6$H$_5$ | m.p.: 84° C. |
| 131 | 0 | (3) —CH$_2$CH$_2$— (5) | (2) Cl | (4) Cl | (3) 1-ethyl-4-methyl-tetrazol-5(4H)-one | C$_6$H$_5$ | |
| 132 | 0 | (3) —CH$_2$CH$_2$— (5) | (2) Cl | (4) Cl | (3) 1,4-diethyl-tetrazol-5(4H)-one | C$_6$H$_5$ | |
| 133 | 0 | (3) —CH$_2$CH$_2$— (5) | (2) Cl | (4) Cl | (3) 1-ethyl-4-vinyl-tetrazol-5(4H)-one | C$_6$H$_5$ | |
| 134 | 0 | (3) —CH$_2$CH$_2$— (5) | (2) Cl | (4) SO$_2$CH$_3$ | (3) 1,4-diethyl-tetrazol-5(4H)-one | C$_6$H$_5$ | |
| 135 | 0 | (3) —CH$_2$CH$_2$— (5) | (2) Cl | (4) SO$_2$CH$_3$ | (3) 4-cyclopropyl-1-ethyl-tetrazol-5(4H)-one | C$_6$H$_5$ | |
| 136 | 0 | (3) —CH$_2$CH$_2$— (5) | (2) Cl | (4) SO$_2$CH$_3$ | (3) 1-ethyl-4-vinyl-tetrazol-5(4H)-one | C$_6$H$_5$ | |

TABLE 2-continued

Further examples of the compounds of the formula (I)

| Ex No. | n | (position) R¹, R2 | (position) R³ | (position) R⁴ | (position) —A-Z | Y | Physical data |
|---|---|---|---|---|---|---|---|
| 137 | 0 | (3) —CH$_2$CH$_2$— (5) | (2) Cl | (4) SO$_2$CH$_3$ | (3) 1-ethyl-4-methyl-tetrazolin-5-one | CH$_3$ | |
| 138 | 0 | (3) —CH$_2$CH$_2$— (5) | (2) Cl | (4) SO$_2$CH$_3$ | (3) 1-ethyl-4-methyl-tetrazolin-5-one | C$_2$H$_5$ | |
| 139 | 0 | (3) —CH$_2$CH$_2$— (5) | (2) Br | (4) Br | (3) 1-ethyl-4-methyl-tetrazolin-5-one | C$_6$H$_5$ | |
| 140 | 0 | (3) —CH$_2$CH$_2$— (5) | (2) Br | (4) Br | (3) 1-ethyl-4-cyclopropyl-tetrazolin-5-one | C$_6$H$_5$ | |
| 141 | 0 | (3) —CH$_2$CH$_2$— (5) | (2) CH$_3$ | (4) SO$_2$CH$_3$ | (3) 1-ethyl-4-methyl-tetrazolin-5-one | C$_6$H$_5$ | |
| 142 | 0 | (3) —CH$_2$CH$_2$— (5) | (2) CH$_3$ | (4) SO$_2$CH$_3$ | (3) 1-ethyl-4-cyclopropyl-tetrazolin-5-one | C$_6$H$_5$ | |
| 143 | 0 | (3) —CH$_2$CH$_2$— (5) | (2) OCH$_3$ | (4) Cl | (3) 1-ethyl-4-methyl-tetrazolin-5-one | C$_6$H$_5$ | |

TABLE 2-continued

Further examples of the compounds of the formula (I)

(I)

| Ex No. | n | (position) R¹, R² | (position) R³ | (position) R⁴ | (position) —A-Z | Y | Physical data |
|---|---|---|---|---|---|---|---|
| 144 | 0 | (3) —CH₂CH₂— (5) | (2) OCH₃ | (4) Cl | (3) [cyclopropyl-ethyl-tetrazinone structure] | C₆H₅ | |

USE EXAMPLES

Example A

Pre-Emergence Test
Solvent: 5 parts by weight of acetone
Emulsifier: 1 part by weight of alkilaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After 24 hours, the soil is sprayed with the preparation of active compound such that the particular amount of active compound desired is applied per unit area. The concentration of active compound in the spray liquor is chosen such that the particular amount of active compound desired is applied in 1000 litres of water per hectare.

After three weeks, the degree of damage to the plants is rated in % damage in comparison to the development of the untreated control. The figures denote:

0%=no effect (like untreated control)
100%=total destruction

In this test, for example, the compound of the Preparation Example 16 exhibits strong activity against weeds, and is tolerated well by some crop plants, such as, for example, maize.

Example B

Post-Emergence Test
Solvent: 5 parts by weight of acetone
Emulsifier: 1 part by weight of alkilaryl polyglycol ether To produce a suitable preparation of active compound, 1 part by weight of active compound is mixed with the stated amount of solvent, the stated amount of emulsifier is added and the concentrate is diluted with water to the desired concentration.

Test plants of a height of 5–15 cm are sprayed with the preparation of active compound such that the particular amounts of active compound desired are applied per unit area. The concentration of the spray liquor is chosen such that the particular amounts of active compound desired are applied in 1000 l of water/ha.

After three weeks, the degree of damage to the plants is rated in % damage in comparison to the development of the untreated control.

The figures denote:

0%=no effect (like untreated control)
100%=total destruction

In this test, for example, the compounds of Preparation Examples 1, 2, 5, 16, 17, 18, 19 and 20 exhibit strong activity against weeds, and they are tolerated well by some crop plants, such as, for example, maize and wheat.

What is claimed is:

1. A substituted benzoylcyclohexenone of the formula (I), (I)

wherein
n represents the number 0, 1 or 2,
A represents a single bond or represents alkanediyl (alkylene) having 1 to 6 carbon atoms,
$R^1$ represents hydrogen, phenyl or optionally cyano-, halogen-, $C_1$–$C_4$-alkoxy- or $C_1$–$C_4$-alkylthio-substituted alkyl having 1 to 6 carbon atoms,
$R^2$ represents hydrogen or optionally cyano-, halogen-, $C_1$–$C_4$-alkoxy- or $C_1$–$C_4$-alkylthio-substituted alkyl having 1 to 6 carbon atoms, or together with $R^1$ represents alkanediyl (alkylene) having 1 to 6 carbon atoms, or together with $R^1$—in this case attached to the same carbon atom—and the carbon atom to which $R^1$ and $R^2$ are attached in this case represents a (C=O) grouping,
$R^3$ represents hydrogen, nitro, cyano, carboxyl, carbamoyl, thiocarbamoyl, halogen, or represents in each case optionally cyano-, halogen- or $C_1$–$C_4$-alkoxy-substituted alkyl, alkoxy, alkylthio, alkylsuiphinyl, alkyl-sulphonyl, alkylamino, dialkylamino or dialkylaminosulphonyl having in each case 1 to 6 carbon atoms in the alkyl groups, $R^4$ represents hydrogen, nitro, cyano, carboxyl, carbamoyl, thiocarbamoyl, halogen, or represents in each case optionally cyano-, halogen- or $C_1$–$C_4$-alkoxy-substituted alkyl, alkoxy, alkylthio, alkylsulphinyl, alkyl-sulphonyl, alkylamino, dialkylamino or dialkylaminosulphonyl having in each case 1 to 6 carbon atoms in the alkyl groups, and Y represents hydrogen, represents optionally cyano-, halogen- or $C_1$–$C_4$-alkoxy-substituted alkyl having 1 to 10 carbon atoms, represents in each case optionally cyano-, halogen-, $C_1$–$C_4$-alkyl-carbonyl- or $C_1$–$C_4$-alkoxy-carbonyl-substituted alkenyl or alkinyl having in each case 2 to 10 carbon atoms, or represents in each case optionally nitro-, amino-, cyano-, carboxyl-, carbamoyl-, thiocarbamoyl-, halogen-, $C_1$–$C_4$-alkyl-, $C_1$–$C_4$-halogenoalkyl-, $C_1$–$C_4$-alkoxy-$C$–$C_4$-alkyl-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkylsulphinyl-, $C_1$–$C_4$-halogenoalkylsulphinyl-, $C_1$–$C_4$-alkylsulphonyl-, $C_1$–$C_4$-halogenoalkylsulphonyl-, $C$–$C_4$-alkyl-carbonyl-, $C$–$C_4$-alkoxy-carbonyl-, $C$–$C_4$-alkyl-carbonyl-amino-, $C_1$–$C_4$-alkoxy-carbonyl-amino-, $C_1$–$C_4$-alkyl-sulphonyl-amino-substituted aryl or arylalkyl having in each case 6 or 10 carbon atoms in the aryl groups and optionally 1 to 4 carbon atoms in the alkyl moiety, and Z represents

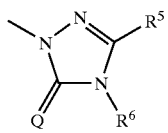

in which

Q represents oxygen or sulphur, $R^5$ represents hydrogen, hydroxyl, mercapto, cyano, halogen, represents in each case optionally cyano-, halogen-, $C_1$–$C_4$-alkoxy, $C_1$–$C_4$-alkylthio-, $C_1$–$C_4$-alkylsulphinyl- or $C_1$–$C_1$-alkylsulphonyl-substituted alkyl, alkylcarbonyl, alkoxy, alkoxycarbonyl, alkylthio, alkylsulphinyl or alkylsulphonyl having in each case up to 6 carbon atoms in the alkyl groups, represents in each case optionally halogen-substituted alkylamino or dialkylamino having in each case up to 6 carbon atoms in the alkyl groups, represents in each case optionally halogen-substituted alkenyl, alkinyl, alkenyloxy, alkenylthio, alkinylthio or alkenylamino having in each case up to 6 carbon atoms in the alkenyl or alkinyl groups, represents in each case optionally halogen-substituted cycloalkyl, cycloalkyloxy, cycloalkylthio, cycloalkylamino, cycloalkylalkyl, cycloalkylalkoxy, cycloalkylalkylthio or cycloalkylalkylamino having in each case 3 to 6 carbon atoms in the cycloalkyl groups and optionally up to 4 carbon atoms in the alkyl moiety, or represents in each case optionally halogen-, $C_1$–$C_1$-alkyl- or $C_1$–$C_4$-alkoxy-substituted phenyl, phenyloxy, phenylthio, phenylamino, benzyl, benzyloxy, benzylthio or benzylamino, represents pyrrolidino, piperidino or morpholino, and $R^6$ represents hydrogen, hydroxyl, amino, alkylideneamino having up to 4 carbon atoms, represents in each case optionally halogen- or $C_1$–$C_4$-alkoxy-substituted alkyl, alkoxy, alkylamino, dialkylamino or alkanoylamino having in each case up to 6 carbon atoms in the alkyl groups, represents in each case optionally halogen-substituted alkenyl, alkinyl or alkenyloxy having in each case up to 6 carbon atoms in the alkenyl or alkinyl groups, represents in each case ontionally halogen-substituted cycloalkyl, cycloalkylalkyl or cycloalkylamino having in each case 3 to 6 carbon atoms in the cycloalkyl groups and optionally up to 3 carbon atoms in the alkyl moiety, or represents in each case optionally halogen-, $C_1$–$C_4$-alkyl- or $C_1$–$C_4$-alkoxy-substituted phenyl or benzyl, or together with an adjacent radical $R^5$ represents optionally halogen- or $C_1$–$C_4$-alkyl-substituted alkanediyl having 3 to 5 carbon atoms, and a tautomer, stereoisomer, salt or metal coordination complex compound of said substituted benzoylcyclohexenone of the formula (I).

2. The substituted benzoylcyclohexenone of the formula (I) according to claim 1, wherein n represents the number 0 or 2, A represents a single bond or represents alkanediyl (alkylene) having 1 to 4 carbon atoms, $R^1$ represents hydrogen, phenyl or optionally cyano-, halogen-, $C_1$–$C_4$-alkoxy- or $C_1$–$C_4$-alkylthio-substituted alkyl having 1 to 5 carbon atoms, $R^2$ represents hydrogen or optionally cyano-, halogen-, $C_1$–$C_4$-alkoxy- or $C_1$–$C_4$-alkylthio-substituted alkyl having 1 to 5 carbon atoms, or together with $R^1$ represents alkanedlyl (alkylene) having 1 to 5 carbon atoms, $R^3$ represents hydrogen, nitro, cyano, carboxyl, carbamoyl, thiocarbamoyl, halogen, or represents in each case optionally cyano-, halogen- or $C_1$–$C_4$-alkoxy-substituted alkyl, alkoxy, alkylthio, alkylsulphinyl, alkyl-sulphonyl, alkylamino, dialkylamino or dialkylaminosulphonyl having in each case 1 to 5 carbon atoms in the alkyl groups, $R^4$ represents hydrogen, nitro, cyano, carboxyl, carbamoyl, thiocarbamoyl, halogen, or represents in each case optionally cyano-, halogen- or $C_1$–$C_4$-alkoxy-substituted alkyl, alkoxy, alkylthio, alkylsulphinyl, alkylsulphonyl, alkylamino, dialkylamino or dialkylaminosulphonyl having in each case 1 to 5 carbon atoms in the alkyl groups, Y represents hydrogen, represents optionally cyano-, halogen- or $C_1$–$C_4$-alkoxy-substituted alkyl having 1 to 6 carbon atoms, represents in each case optionally cyano-, halogen-, $C_1$–$C_4$-alkyl-carbonyl- or $C_1$–$C_4$-alkoxy-carbonyl-substituted alkenyl or alkinyl having in each case 2 to 6 carbon atoms, or represents in each case optionally nitro-, amino-, cyano-, carboxyl-, carbamoyl-, thiocarbamoyl-, halogen-, $C_1$–$C_4$-alkyl-, $C_1$–$C_4$-halogenoalkyl-, $C_1$–$C_4$-alkoxy-$C_1$–$C_4$-alkyl-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkylsulphinyl-, $C_1$–$C_4$-halogenoalkylsulphinyl-, $C_1$–$C_4$-alkylsulphonyl-, $C_1$–$C_4$-halogenoalkylsulphonyl-, $C_1$–$C_4$-alkyl-carbonyl-, $C_1$–$C_4$-alkoxy-carbonyl-, $C_1$–$C_4$-alkyl-carbonyl-amino-, $C_1$–$C_4$-alkoxy-carbonyl-amino-, $C_1$–$C_4$-alkyl-sulphonyl-amino -substituted aryl or arylalkyl having in each case 6 or 10 carbon atoms in the aryl groups and optionally 1 to 4 carbon atoms in the alkyl moiety, Q represents oxygen or sulphur, $R^5$ represents hydrogen, hydroxyl, mercapto, cyano, halogen, represents in each case optionally cyano-, halogen-, $C_1$–$C_4$-alkoxy-, $C_1$–$C_4$-alkyl-thio-, $C_1$–$C_4$-alkylsulphinyl- or $C_1$–$C_4$-alkylsulphonyl-substituted alkyl, alkylcarbonyl, alkoxy, alkoxycarbonyl, alkylthio, alkylsulphinyl or alkylsulphonyl having in each case up to 6 carbon atoms in the alkyl groups, represents in each case optionally halogen-substituted alkylamino or dialkylamino having in each case up to 6 carbon atoms in the alkyl groups, represents in each case optionally halogen-substituted alkenyl, alkinyl, alkenyloxy, alkenylthio, alkinylthio or alkenylamino having in each case up to 6 carbon atoms in the alkenyl or alkinyl groups, represents in each case optionally halogen-substituted cycloalkyl, cycloalkyloxy, cycloalkylthio, cycloalkylamino, cycloalkylalkyl, cycloalkylalkoxy, cycloalkylalkylthio or cycloalkylalkylamino having in each case 3 to 6 carbon atoms in the cycloalkyl groups and optionally up to 4 carbon atoms in the alkyl moiety, or represents in each case optionally halogen-, $C_1$–$C_4$-alkyl- or $C_1$–$C_4$-alkoxy-substituted phenyl, phenyloxy, phenylthio, phenylamino, benzyl, benzyloxy, benzylthio or benzylamino, represents pyrrolidino, piperidino or morpholino, and $R^6$ represents hydrogen, hydroxyl, amino, alkylideneamino having up to 4 carbon atoms, represents in each case optionally halogen- or $C_1$–$C_4$-alkoxy-substituted alkyl, alkoxy, alkylamino, dialkylamino or alkanoylamino having in each case up to 6 carbon atoms in the alkyl groups, represents in each case optionally halogen-substituted alkenyl, alkinyl or alkenyloxy having in each case up to 6 carbon atoms in the alkenyl or alkinyl groups, represents in each case optionally halogen-substituted cycloalkyl, cycloalkylalkyl or cycloalkylamino having in each case 3 to 6 carbon atoms in the cycloalkyl groups and optionally up to 3 carbon atoms in the alkyl moiety, or represents in each case optionally halogen-, $C_1$–$C_4$-alkyl- or $C_1$–$C_4$-alkoxy-substituted phenyl or benzyl, or together with an adjacent radical $R^5$ represents optionally halogen- or $C_1$–$C_4$-alkyl-substituted alkanediyl having 3 to 5 carbon atoms.

3. The substituted benzoylcyclohexenone of the formula (I), according to claim 1 wherein A represents a single bond or represents methylene, ethylidene (ethane-1,1-diyl) or dimethylene (ethane-1,2-diyl), $R^1$ represents hydrogen, phenyl or in each case optionally cyano-, fluorine-chlorine-, bromine-, methoxy-, ethoxy-, n- or i-propoxy-, methylthio, ethylthio-, n- or i-propylthio-substituted methyl, ethyl, n- or i-propyl, n-, i-or s-butyl, $R^2$ represents hydrogen or represents in each case optionally cyano-, fluorine-, chlorine-, bromine-, methoxy-, ethoxy-, n- or i-propoxy-, methylthio-, ethylthio-, n- or i-propylthio-substituted methyl, ethyl, n- or i-propyl, n-, i- or s-butyl, or together with $R^1$ represents methylene, ethylidene (ethane-1,1-diyl), dimethylene (ethane-1,2-diyl), propylidene (propane-1,1-diyl) or trimethylene (propane-1,3-diyl), $R^3$ represents hydrogen, nitro, cyano, carboxyl, carbamoyl, thiocarbamoyl, fluorine, chlorine, bromine, iodine, or represents in each case optionally cyano-, fluorine-, chlorine-, bromine-, methoxy-, ethoxy-, n- or i-propoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, n-, i-, s- or t-butylamino, dimethylamino, diethylamino, dimethylaminosulphonyl or diethylaminosulphonyl, $R^4$ represents hydrogen, nitro, cyano, carboxyl, carbamoyl, thiocarbamoyl, fluorine, chlorine, bromine, iodine, or represents in each case optionally cyano-, fluorine-, chlorine-, bromine-, methoxy-, ethoxy-, n- or i-propoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsuiphinyl, ethylsuiphinyl, n- or i-propylsulphinyl, methylsulphonyl, ethylsulphonyl, n- or i-propylsulphonyl, methylamino, ethylamino, n- or i-propylamino, n-, i-, s- or t-butylamino, dimethylamino, diethylamino, dimethylaminosulphonyl or diethylaminosulphonyl, Y represents hydrogen, represents in each case optionally cyano-, fluorine-, chlorine-, bromine-, methoxy-, ethoxy-, n- or i-propoxy-substituted methyl, ethyl, n- or i-propyl, n-, i-, s- or t-butyl, represents in each case optionally cyano-, fluorine-, chlorine-, bromine-, acetyl-, propionyl-, n- or -butyroyl-, methoxycarbonyl-, ethoxycarbonyl-, n- or i-propoxycarbonyl-substituted ethenyl, propenyl, butenyl, pentenyl, ethinyl, propinyl or butinyl, or represents in each case optionally nitro-, amino-, cyano-, carboxyl-, carbamoyl-, thiocarbamoyl-, fluorine-, chlorine-, bromine-, iodine-, methyl-, ethyl-, n- or i-propyl-, n-, i-, s- or t-butyl-, trifluoromethyl-, methoxymethyl-, ethoxymethyl-, methoxyethyl-, ethoxyethyl-, methoxy-, ethoxy-, n- or i-propoxy-, n-, i-, s- or t-butoxy-, difluoromethoxy-, trifluoromethoxy-, methylthio-, ethylthio-, n- or i-propylthio-, n-, i-, s- or t-butylthio-, difluoromethylthio-, trifluoromethylthio-, methylsulphinyl-, ethylsulphinyl-, trifluoromethylsulphinyl-, methylsulphonyl-, ethylsulphonyl-, trifluoromethylsulphonyl-, acetyl-, propionyl-, n- or i-butyroyl-, methoxycarbonyl-, ethoxycarbonyl-, n- or i-propoxycarbonyl-, acetylamino-, propionylamino-, methoxycarbonylamino-, ethoxycarbonylamino-, methylsulphonylamino-, ethylsulphonylamino-, n- or i-propylsulphonyl-amino-substituted phenyl, naphthyl, benzyl or phenylethyl, Q represents oxygen, $R^5$ represents hydrogen, hydroxyl, mercapto, cyano, fluorine, chlorine, bromine, iodine, represents in each case optionally fluorine-, chlorine-, methoxy-, ethoxy-, n- or i-propoxy-, n-, i-, s- or t-butoxy-, methylthio-, ethylthio-, n- or i-propylthio-, n-, i-, s- or t-butylthio-, methylsuiphinyl-, ethylsuiphinyl-, n- or i-propylsulphinyl-, methylsulphonyl-, ethylsulphonyl-, n- or i-propyl-sulphonyl-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsuiphinyl, ethylsuiphinyl, n- or i-propylsulphinyl, methylsulphonyl, ethylsulphonyl, n- or i-propylsulphonyl, represents methylamino, ethylamino, n- or i-propylamino, n-, i-, s- or t-butylamino, dimethylamino, diethylamino, di-n-propylamino or di-i-propylamino, represents in each case optionally fluorine- and/or chlorine-substituted ethenyl, propenyl, butenyl, ethinyl, propinyl, butinyl, propenyloxy, butenyloxy, propenylthio, butenylthio, propenylamino or butenylamino, represents in each case optionally fluorine- and/or chlorine-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino, cyclohexylamino, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopropylmethylthio, cyclobutylmethylthio, cyclopentylmethyithio, cyclohexylmethylthio, cyclopropylmethylamino, cyclobutylmethylamino, cyclopentylmethylamino or cyclohexylmethylamino, or represents in each case optionally fluorine-, chlorine-, methyl-, ethyl-, n- or i-propyl-, n-, i-, s- or t-butyl-, methoxy-, ethoxy-, n- or i-propoxy-substituted phenyl, phenyloxy, phenylthio, phenylamino, benzyl, benzyloxy, benzylthio or benzylamino, and $R^6$ represents hydrogen, hydroxyl, amino, represents in each case optionally fluorine- and/or chlorine-, methoxy- or ethoxy-substituted methyl, ethyl, n- or i-propyl, n-, i- or s-butyl, methoxy, ethoxy, n- or i-propoxy, methylamino, ethylamino or dimethylamino, represents in each case optionally fluorine- and/or chlorine-substituted ethenyl, propenyl, ethinyl, propinyl or propenyloxy, represents in each case optionally fluorine- and/or chlorine-substituted cyclopropyl, cyclobutyl, cyclopentyl, cyclohexyl, cyclopropylmethyl, cyclobutylmethyl, cyclopentylmethyl or cyclohexylmethyl, or represents in each case optionally fluorine-, chlorine-, methyl-, ethyl-, n- or i-propyl-, n-, i-, s- or t-butyl-, methoxy-, ethoxy-, n- or i-propoxy-substituted phenyl or benzyl, or together with an adjacent radical $R^5$ represents in each case optionally methyl- and/or ethyl-substituted propane-1,3-diyl (trimethylene), butane-1,4-diyl (tetramethylene) or pentane-1,5-diyl (pentamethylene).

4. The substituted benzoylcyclohexenone of the formula (I) according to claim 1 wherein A represents a single bond or represents methylene, $R^1$ represents hydrogen, phenyl or in each case optionally fluorine- or chlorine-substituted methyl, ethyl, n- or i-propyl, $R^2$ represents hydrogen or in each case optionally fluorine- or chlorine-substituted methyl, ethyl, n- or i-propyl, or together with $R^1$ represents methylene or dimethylene, $R^3$ represents hydrogen, nitro, cyano, fluorine, chlorine, bromine, iodine, or represents in each case optionally fluorine-, chlorine-, methoxy- or ethoxy-substituted methyl, ethyl, n- or i-propyl, methoxy, ethoxy, methylthio, ethylthio, methylsulphinyl, ethylsulphinyl, methylsulphonyl, ethylsulphonyl, methylamino, ethylamino, dimethylamino or dimethylaminosulphonyl, $R^4$ represents hydrogen, nitro, cyano, fluorine, chlorine, bromine, iodine, or represents in each case optionally fluorine-, chlorine-, methoxy- or ethoxy-substituted methyl, ethyl, n- or i-propyl, methoxy, ethoxy, methylthio, ethylthio, methylsulphinyl, ethylsulphinyl, methylsulphonyl, ethylsulphonyl, methylamino, ethylamino, dimethylamino or dimethylaminosulphonyl, Y represents hydrogen, represents in each case optionally cyano-, fluorine-, chlorine-, bromine-, methoxy-, ethoxy-, n- or i-propoxy-substituted methyl, ethyl, n- or i-propyl, n-, i-, s- or t-butyl, represents in each case optionally fluorine-, chlorine- or bromine-substituted propenyl, butenyl, pentenyl, propinyl or butinyl, or represents in each case optionally nitro-, amino-, cyano-, fluorine-, chlorine-, bromine-, methyl-, ethyl-, n- or i-propyl-, n-, i-, s- or t-butyl-, trifluoromethyl-, methoxymethyl-, ethoxymethyl-, methoxyethyl-, ethoxyethyl-, methoxy-, ethoxy-, n- or i-propoxy-, difluoromethoxy-, trifluoromethoxy-, methylthio-, ethylthio-, n- or i-propylthio-, difluoromethylthio-, trifluoro-methylthio-, methylsuiphinyl-, ethylsulphinyl-, trifluoromethylsulphinyl-, methylsulphonyl, ethylsulphonyl-, trifluoromethylsulphonyl-, acetyl-, propionyl-, methoxycarbonyl-, ethoxycarbonyl-, acetylamino-, propionylamino-, methoxycarbonylamino-, ethoxycarbonylamino-, methylsulphonylamino- or ethylsulphonylamino-substituted phenyl or benzyl, $R^5$ represents hydrogen, fluorine, chlorine, bromine, represents in each case optionally fluorine-, chlorine-, methoxy-, ethoxy-, n- or i-propoxy-, methylthio-, ethylthio-, methylsulphinyl-, ethylsulphinyl-, methylsulphonyl-, ethylsulphonyl-substituted methyl, ethyl, n- or i-propyl, n-, i- or s-butyl, methoxy, ethoxy, n- or i-propoxy, n-, i- or s-butoxy, methylthio, ethylthio, n- or i-propylthio, n-, i- or s-butylthio, methylsulphinyl, ethylsuiphinyl, n- or i-propylsuiphinyl, methylsulphonyl, ethylsulphonyl, n- or i-propylsulphonyl, represents methylamino, ethylamino, n- or i-propylamino, n-, i- or s-butylamino, dimethylamino or diethylamino, represents in each case optionally fluorine- and/or chlorine-substituted ethenyl, propenyl, butenyl, ethinyl, propinyl, butinyl, propenyloxy, butenyloxy, propenylthio or represents in each case optionally fluorine- and/or chlorine-substituted cyclopropyl, cyclopropyloxy, cyclopropylthio, cyclopropylamino, cyclopropylmethyl, cyclopropylmethoxy, cyclopropylmethylthio or cyclopropylmethylamino, and $R^6$ represents hydrogen, represents amino, represents in each case optionally fluorine- and/or chlorine-, methoxy- or ethoxy-substituted methyl, ethyl, methoxy, ethoxy, methylamino or ethylamino, represents dimethylamino, or represents in each case optionally fluorine- and/or chlorine-substituted cyclopropyl, cyclopropylmethyl, phenyl or benzyl, or together with an adjacent radical $R^5$ represents in each case optionally methyl- and/or ethyl-substituted propane-1,3-diyl (trimethylene), butane-1,4-diyl (tetramethylene) or pentane-1,5-diyl (pentamethylene).

5. The substituted benzoylcyclohexenone of the formula (I) according to claim 1, wherein $R^1$ represents hydrogen, $R^2$ represents hydrogen, $R^3$ represents chlorine, tnfluoromethyl or methoxy, $R^4$ represents chlorine, tnfluoromethyl or methylsulphonyl, $R^5$ represents hydrogen, methyl or ethyl, and $R^6$ represents hydrogen, methyl, ethyl, n- or i-propyl, n-, i-, s- or t-butyl, cyclopropyl, cyclopropylmethyl, cyclopentyl, cyclopentylmethyl, cyclohexyl, cyclohexylmethyl, phenyl or benzyl.

6. The substituted benzoylcyclohexenone of the formula (I) according to claim 1 wherein $R^5$ represents hydrogen, and $R^6$ represents methyl, ethyl, n- or i-propyl, n-, i-, s- or t-butyl, cyclopropyl, cyclopropylmethyl or phenyl.

7. The substituted benzoylcyclohexenone of the formula (I) according to claim 1 wherein n represents the number 0.

8. The substituted benzoylcyclohexenone of the formula (I) according to claim 1 wherein Q represents oxygen.

9. The substituted benzoylcyclohexenone of the formula (I) according claim 1 wherein Y represents hydrogen, represents in each case optionally fluorine-, chlorine- or methoxy-substituted methyl, ethyl, n- or i-propyl, n-, i-, s- or t-butyl, represents in each case optionally fluorine- or chlorine-substituted propenyl butenyl, pentenyl or represents optionally amino-, cyano-, fluorine-, chlorine-, methyl-, ethyl-, trifluoromethyl-, methoxy- or ethoxy-substituted phenyl.

10. A substituted benzoylcyclohexenone of the formula (IA)

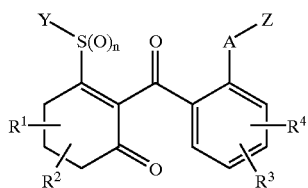

wherein n, A, $R^1$, $R^2$, $R^3$, $R^4$, Y and Z are as defined in claim 1.

11. A substituted benzoylcyclohexenone of the formula (IB)

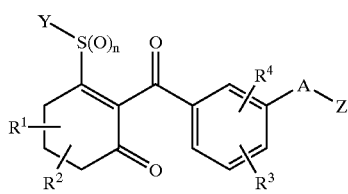

wherein n, A, $R^1$, $R^2$, $R^3$, $R^4$, Y and Z are as defined in claim 1.

12. A substituted benzoylcyclohexenone of the formula (IC)

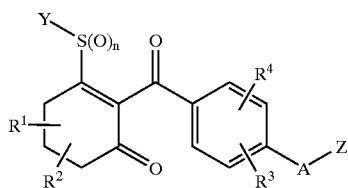

wherein n, A, $R^1$, $R^2$, $R^3$, $R^4$, Y and Z are as defined in claim 1.

13. A sodium, potassium, magnesium, calcium, ammonium, $C_1$–$C_4$-alkyl-ammonium, di-($C_1$–$C_4$-alkyl)-ammonium, tri-($C_1$–$C_4$-alkyl)-ammonium-, tetra-($C_1$–$C_4$-alkyl)-ammonium, tri-($C_1$–$C_4$-alkyl)-sulphonium, $C_5$- or $C_6$-cycloalkyl-ammonium and di-($C_1$–$C_2$-alkyl)-benzyl-ammonium salt of said substituted benzoylcyclohexenone of the formula (I) according to claim 1, and one or more complex compound comprising said salt with one or more metals, wherein said metals are optionally selected from the group consisting of copper, iron, cobalt, and nickel.

14. A process for preparing a substituted benzoylcyclohexenone according to claim 1 comprising:

reacting a compound of the formula (II)

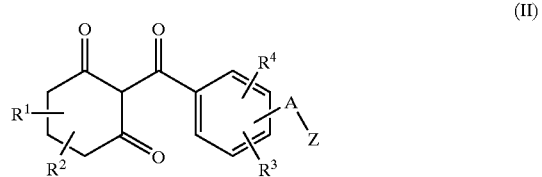

wherein

A, $R^1$, $R^2$, $R^3$, $R^4$ and Z are as defined in claim 1 with a halogenating agent, optionally in the presence of a reaction auxiliary and optionally in the presence of a diluent to obtain a halogenocyclohexenone of the formula (III)

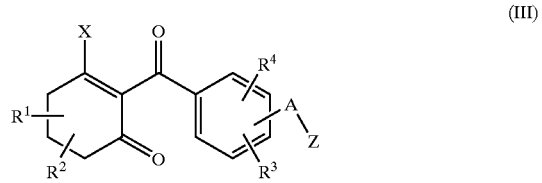

wherein

A, $R^1$, $R^2$, $R^3$, $R^4$ and Z are as defined in claim 1 and

X represents halogen, and in a second step, either after intermediate isolation or without intermediate isolation ("in situ") of said halogenocyclohexenone of the formula (III), reacting said halogenocyclohexenone of the formula (III) in said second step with a mercapto compound of the formula (IV)

wherein

Y is as defined in claim 1, optionally in the presence of a reaction auxiliary and optionally in the presence of a diluent to obtain said substituted benzoylcyclohexenone of the formula (I).

15. A herbicidal composition comprising at least one substituted benzoylcyclohexeneone according to claim 1 and one or more extenders.

16. A method for controlling undesirable plants, comprising allowing an effective amount of at least one substituted benzoylcyclohexenone according to claim 1 or a herbicidal composition according to claim 15 to act on one or more undesirable plants and/or their habitat.

* * * * *